US009943048B2

(12) United States Patent
Jinushi et al.

(10) Patent No.: US 9,943,048 B2
(45) Date of Patent: Apr. 17, 2018

(54) METHOD FOR PRODUCING RICE F1 SEED, RICE F1 SEED, AND RICE MALE STERILE LINE

(75) Inventors: Kenji Jinushi, Nagoya (JP); Yoichi Morinaka, Nagoya (JP); Tomonori Takashi, Kisarazu (JP); Hidemi Kitano, Nagoya (JP); Toshiro Komura, Okazaki (JP)

(73) Assignee: Honda Motor Co., Ltd., Tokyo (JP)

( * ) Notice: Subject to any disclaimer, the term of this patent is extended or adjusted under 35 U.S.C. 154(b) by 374 days.

(21) Appl. No.: 13/421,630

(22) Filed: Mar. 15, 2012

(65) Prior Publication Data

US 2012/0246756 A1   Sep. 27, 2012

(30) Foreign Application Priority Data

Mar. 18, 2011   (JP) .................. 2011-061396

(51) Int. Cl.
   A01H 5/10   (2018.01)
   A01H 1/02   (2006.01)

(52) U.S. Cl.
   CPC .............. A01H 1/02 (2013.01); A01H 5/10 (2013.01)

(58) Field of Classification Search
   USPC .................... 800/260, 320.2, 295
   See application file for complete search history.

(56) References Cited

U.S. PATENT DOCUMENTS

| | | | |
|---|---|---|---|
| 6,512,167 | B1 | 1/2003 | Carolo |
| 7,417,180 | B2 | 8/2008 | Ashikari et al. |
| 8,030,561 | B2 | 10/2011 | Takashi et al. |

FOREIGN PATENT DOCUMENTS

| | | | |
|---|---|---|---|
| CN | 1489895 | A | 4/2004 |
| CN | 1951172 | A | 4/2007 |
| JP | 2000-139465 | A | 5/2000 |
| JP | 2004-024126 | A | 1/2004 |
| JP | 2005-110623 | A | 4/2005 |
| JP | 2007-054020 | A | 3/2007 |
| JP | 3949637 | B2 | 7/2007 |
| JP | 2008-283902 | A | 11/2008 |
| JP | 4248881 | B2 | 4/2009 |
| JP | 4352102 | B1 | 10/2009 |
| JP | 4368391 | B2 | 11/2009 |
| JP | 2010-011826 | A | 1/2010 |
| JP | 2010-011826 | A | 1/2010 |
| JP | 2010-011842 | A | 1/2010 |
| JP | 2010-011867 | A | 1/2010 |
| JP | 4409610 | B2 | 2/2010 |
| WO | WO 02/085105 | A2 | 10/2002 |
| WO | WO 03/070934 | A1 | 8/2003 |
| WO | 2004/113537 | A1 | 12/2004 |
| WO | WO 2010/067801 | A1 | 6/2010 |

OTHER PUBLICATIONS

Ookawa et al. Nature Communication (2010), pp. 1-11.*
Ashikari et al. Science (2005), vol. 309, pp. 741-745.*
Asano, et al., "Genetic and Molecular Analysis of Utility of sdl Alleles in Rice Breeding", 2007, Breeding Science 57, pp. 53-58.
Ashikari, et al., "Cytokinin oxidase regulates rice grain production", 2005, Science 309, pp. 741-745.
Chinese Office Action, Chinese Patent Application No. 201210073413.3 dated Aug. 15, 2013.
Gu, et al., "Grain quality of hybrid rice: genetic variation and molecular improvement", 2010, Accelerating Hybrid rice development, Edited by Xie and Hardy, pp. 345-356.
H. Yamane, et al., Comparative study on the genomic sequence of grain productivity related gene Gn Ia regions among the gunus Oryza, thremmatology study (Additional vol. 2) 2007 pp. 307.
K. Maruyama, "Thremmatological Studies on First Filial Generation Rice Cultivar", Doctoral Dissertation of University of Tokyo (Feb. 14, 1993), pp. 67.
Kato, et al., "Hybrid rice research in Japan", 1994, Hybrid Rice Technology—new development and future prospects, Edited by Virmani, pp. 149-156.
Kumar, et et al., "Genetic analysis of waxy loculocusrice (*Oryza sativa* L.)", 1987, Theor. Appl. Genet. 73, pp. 481-488.
Kumar, et al., "Inheritance of amylose content in rice (*Oryza sativa* L.)", 1988, Euphytica, 38, pp. 261-269.
Liu, et al., "Improvement of resistance to rice blast in Zhenshan 97 by inolecular inarker-aided selection", 2003, Acta Botanica Sinica 45, pp. 1346-1350.
Luo, et al., "Analysis of photoperiod-sensitivity genes in Minghui 63, an restorer line of indica rice (*Oryza sativa* L.)", 2003, Yi Chuan Xue Bao 30, pp. 804-810.
M. Miyata, et al., "Marker-assisted selection and evaluation of the QTL for stigma exsertion under japonica rice genetic background", 2006, Thor. Appl. Gent. 114, pp. 539-548.
Monna, et al., "Positional cloning of rice semidwarfing gene, sd-1:rice, "green revolution gene" encodes a mutant enzyme involved in gibberellin synthesis", 2002, DNA Res. 9, pp. 11-17.
N. Hayashi, et al., "Durable panicle blast-resistance gene Pb1 encodes an atypical CC-NBS-LRR protein and was generated by acquiring a promoter through local genome duplication", 2010, Plant J. 64, pp. 498-510.
Niroula, et al., "Ploidy level and phenotypic dissection of Nepalese wild species of rice", 2005, Scientific World 3, pp. 78-84.
Notification (Information Statement), Japanese Patent Application No. 2012-059239 dated Nov. 26, 2013.

(Continued)

*Primary Examiner* — Medina A Ibrahim
(74) *Attorney, Agent, or Firm* — Carrier Blackman & Associates, P.C.; Joseph P. Carrier; Fulchand P. Shende

(57) ABSTRACT

Provided is a method for producing a rice F1 seed, including crossing a rice male sterile line of Koshihikari containing one or more genes selected from the group consisting of the sd1 gene, the Gn1 gene and the hd1 gene derived from *Oryza sativa* L. cultivar Habataki, or a rice male sterile line exhibiting semi-waxiness as a seed parent, with a rice fertility restorer line as a pollen parent, and collecting the first filial generation seed (F1 seed) from the post-crossing seed parent; and a rice male sterile line containing one or more genes selected from the group consisting of the sd1 gene, the Gn1 gene and the hd1 gene derived from *Oryza sativa* L. cultivar Habataki.

8 Claims, 9 Drawing Sheets

(56) References Cited

OTHER PUBLICATIONS

Sugiura, et al., "Molecular Marker-assisted Selection in a Recurrent Backcross Breeding for the Incorporation of Resistance to Rice Stripe Virus and Panicle Blast in Rice (*Oryza sativa* L.)", Breeding Research 6: pp. 143-148, 2004.
Suzuki, Yasuhiro: "Fluctuation of amylose content in rice seeds—mechanism and regulation—" "Agriculture and Horticulture", vol. 81 (2006), pp. 183-190.
Xu et al., "Analysis of heading time genotype for a rice photoperiod and thermo-sensitive male sterile line PeiAi64S", 2005, Yi Chuan Xue Bao 32, pp. 57-65.
Yano, et al., "Hd1, a major photoperiod sensitivity quantitative trait locus in rice, is closely related to the *Arabidopsis* flowering time gene CONSTANS," 2000, Plant Cell 12, pp. 2473-2483.
Yuan, "Hybrid rice breeding in China", 1998, Advancing Hybrid Rice Technology, Editied by Virmani, Siddiq, Muralidharan, pp. 27-33.
Suzuki, Yasuhiro, "Fluctuation of amylose content in rice seeds—climate and regulation—", Agriculture and Horticulture, vol. 81 (2006), pp. 183-190.
United States Office Action, dated May 9, 2014, corresponding to U.S. Appl. No. 13/422,610.
U.S. Office Action dated Oct. 23, 2014 issued in co-pending U.S. Appl. No. 13/422,610.
Office Action dated Feb. 25, 2015, issued in CN Patent Application 201210068896.8 and the English translation thereof.
Li Ping et al., "Psysiological Bases of High Yielding Heterosis in Indica-type F1 Hybrid Rice", Scientia Agricultura Sinica, vol. 23 (5), pp. 39-44.
Office Action issued in corresponding Japanese Patent Application 2012-059239 dated Jan. 19, 2016 with the English translation thereof.
Office Action issued in corresponding Japanese Patent Application 2012-059240 dated Jan. 19, 2016 with the English translation thereof.

* cited by examiner

■ HABATAKI-DERIVED CHROMOSOME FRAGMENT
☐ KOSHIHIKARI-DERIVED CHROMOSOME FRAGMENT

■ HABATAKI-DERIVED CHROMOSOME FRAGMENT
☐ KOSHIHIKARI-DERIVED CHROMOSOME FRAGMENT

■ HABATAKI-DERIVED CHROMOSOME FRAGMENT
▢ KOSHIHIKARI-DERIVED CHROMOSOME FRAGMENT

■ HABATAKI-DERIVED CHROMOSOME FRAGMENT
▢ KOSHIHIKARI-DERIVED CHROMOSOME FRAGMENT

METHOD FOR PRODUCING RICE F1 SEED, RICE F1 SEED, AND RICE MALE STERILE LINE

CROSS-REFERENCE TO RELATED APPLICATION

This Application claims priority to Japanese Application No. 2011-061396, filed Mar. 18, 2011; the disclosure of which is hereby incorporated in its entirety by reference.

SEQUENCE LISTING

The instant application contains a Sequence Listing which has been submitted in ASCII format via EFS-Web and is hereby incorporated by reference in its entirety. Said ASCII copy, created on Apr. 12, 2012, is named 10743928.txt and is 13,440 bytes in size.

The subject seeds for male rice line CMS-Koshihikari eichi 2go have the accession number FERM ABP-22217 and for male rice line CMS-Koshihikari kazusa 3go have the accession number FERM ABP-22218, having both been deposited on Jul. 23, 2014. All restrictions upon availability to the public will be irrevocably removed upon granting of a patent.

BACKGROUND OF THE INVENTION

Field of the Invention

The present invention relates to a rice male sterile line having a favorable characteristic, a method for producing a rice F1 seed using the same rice male sterile line, and a rice F1 seed which is obtained by the same method.

Description of Related Art

In recent years, remarkable advancements in genome analysis techniques have enabled great improvements to be made to crop production. In particular, a DNA marker technique has showed marked progress and the construction of a new cultivar having a beneficial characteristic has become possible through such a technique. For example, up to now, tomatoes having a resistance to *Botrytis cinerea* (for example, see Patent Document 1) or rice plants (*Oryza sativa*) having improvements in lodging resistance and brown rice kernel size (for example, see Patent Document 2) have been created using DNA markers.

Further, through the use of DNA markers and the substitution of chromosome regions including valuable alleles of important genes identified hitherto, specific improvement of a desired characteristic has become possible without significant effect on a large number of other characteristics (for example, see Patent Document 3). For example, as for a rice plant, a rice plant having improvements in culm length (chromosome region in the proximity of sd1 gene), days to heading (chromosome region in the proximity of hd1 gene), number of grains per spike (chromosome region in the proximity of Gn1 gene) or the like has been created (for example, see Patent Document 4). When the sd1 gene in a chromosome of *Oryza sativa* L. cultivar Koshihikari is substituted with the sd1 gene derived from Habataki, a culm length becomes significantly shorter than *Oryza sativa* L. cultivar Koshihikari and a lodging resistance is improved. Further, when the Gn1 gene in a chromosome of *Oryza sativa* L. cultivar Koshihikari is substituted with the Gn1 gene derived from Habataki, a grain density becomes higher than *Oryza sativa* L. cultivar Koshihikari. When the hd1 gene in a chromosome of *Oryza sativa* L. cultivar Koshihikari is substituted with the hd1 gene derived from Habataki, this results in conversion to earlier growth than in *Oryza sativa* L. cultivar Koshihikari.

As for a method of creating a crop having a superior characteristic, there is an F1 hybrid breeding method in which a seed parent is deprived of an ability to synthesize pollen by using a male sterile cytoplasm or the like, whereby crossing between distantly-related lines is realized and the resulting hybrid seed is used as a cultivar. For example, with regard to Lactuca sativa, a Lactuca sativa male sterile line that can be used as a seed parent in an F1 hybrid breeding method has been created (for example, see Patent Document 5).

The F1 hybrid breeding method is used as a technique which is capable of improving yield performance to a very high level with ease by taking advantage of heterosis. Also in breeding of rice plants in Japan, application of the F1 hybrid breeding method has been attempted since the discovery of practical cytoplasmic male-sterility in 1970. In this connection, there is a history that the F1 hybrid breeding method has gradually lost its application due to the fact that taste quality of the line of rice plants reared at that time was not sufficiently high, and a need regarding the high-yielding ability of a rice plant during the rice oversupply period since then is lower.

However, increasing a yield potential of crops has recently become important again in terms of increasing production of food, cultivation costs, and efficient utilization of input energy during cultivation, and will become a more important breeding goal from now on. Further, enlarging a plant itself through the enhancement of productive capacity leads to an increase in productivity of crop residues attracting attention as a raw material of bioethanol of the second generation, and through relative reduction of an amount of GHG discharged in the course of growing processes of crops, may also contribute to a solution to energy problems and environmental problems.

Under the present circumstances in which an improvement of a yield potential has become considered important, an F1 hybrid breeding technique has increasingly gained interest. With regard to an F1 hybrid breeding method, there is a need to create F1 hybrids between large numbers of lines for a candidate line to be selected in a combinatorial test, and therefore the selection of a male sterile line serving as a seed parent has become highly important so as to maintain high efficiency of selection.

*Oryza sativa* L. cultivar Koshihikari, which is the leading variety in Japan, is evaluated highly regarding taste quality, and the line obtained using Koshihikari as a rearing seed parent has a large number of lines with good taste quality. In addition to taste quality, as shown by the fact that it is most widely cultivated in Japan, Koshihikari has adaptability of cultivation over a wide area and exhibits a great number of excellent characteristics such as germination of strong shoots. Further, since Koshihikari has been used as a study subject in a variety of experiments, Koshihikari has an accumulation of scientific knowledge and has an advantage from the viewpoint that it is easy to find leads for improvement. Taken together, it can be said that Koshihikari is one of the most promising lines in rearing of a seed parent of an F1 hybrid.

Further, with regard to taste quality for which there has been difficulty in term of specifically improving such a characteristic until now, improvement of rice quality became possible through lowering of an amylose content and enhancement of rice glutinosity by taking advantage of a semi-waxiness mutant characteristic. Many rice with semi-waxiness exhibit white turbidity of an endosperm thereof and therefore may be easily distinguished from common rice. Among semi-waxiness mutations reported in the past, there are variations in which 7 different du loci are involved, in addition to a variation of the wx gene which is believed to have the most significant influence on an amylose content (for example, see Non Patent Document 1)

PRIOR ART DOCUMENTS

Patent Documents

Patent Document 1: Japanese Patent No. 4248881
Patent Document 2: Japanese Patent No. 4368391
Patent Document 3: Japanese Patent No. 4409610
Patent Document 4: Japanese Patent No. 4352102
Patent Document 5: Japanese Patent No. 3949637

Non Patent Documents

Non Patent Document 1: Suzuki, Yasuhiro: "Fluctuation of amylose content in rice seeds—mechanism and regulation—", "Agriculture and Horticulture", vol. 81 (2006), pp 183-190.

SUMMARY OF THE INVENTION

However, where an F1 hybrid is reared using Koshihikari as one parent, problems frequently occur. For example, in a combinatorial test with a breeding line including *Indica* species, which is distantly related to Koshihikari, the conversion into a late-maturing or long-culm individual occurs, which consequently results in frequent appearance of a line devoid of competence as a line for practical use, and significant deterioration in efficiency of selection.

Further, although an F1 hybrid exhibits improvement of yield performance due to heterosis, since a yield potential of Koshihikari itself is not sufficiently high as compared to common high-yielding lines, a proportion obtaining high-yielding lines possibly suitable for selection is not high. To cope with this, for example, it is preferable to further improve the yield potential of Koshihikari by increasing the number of grains per spike of Koshihikari or other means.

Further, where an F1 hybrid is reared, generally, in order to obtain more potent heterosis, it is necessary to employ a distantly-related line having a taste quality inferior to Koshihikari as one parent. When a distantly-related line is used as one parent, in many cases, this results in inheritance of inferior characteristics regarding the taste quality that the distantly-related line has, and significant lowering of efficiency of selection.

An object of the present invention is to provide a male sterile line of Koshihikari which is highly suitable in an F1 hybrid breeding method, and a method for producing a rice F1 seed using the same rice male sterile line.

As a result of extensive and intensive studies to solve the above-mentioned problems, the present inventors have found that a superior F1 hybrid can be more efficiently created by using a male sterile line with improvement of a specific characteristic through partial substitution of the chromosome thereof with a chromosome fragment derived from a foreign cultivar or mutagenesis as a seed parent. The present invention has been completed based on this finding.

Specifically, the present invention provides:

(1) A method for producing a rice F1 seed, including crossing a rice male sterile line containing one or more genes selected from the group consisting of the sd1 gene derived from *Oryza sativa* L. cultivar Habataki, the Gn1 gene derived from *Oryza sativa* L. cultivar Habataki, and the hd1 gene derived from *Oryza sativa* L. cultivar Habataki, or a rice male sterile line exhibiting semi-waxiness as a seed parent, with a rice fertility restorer line as a pollen parent, and collecting the first filial generation seed (F1 seed) from the post-crossing seed parent, (2) The method for producing a rice F1 seed according to (1), wherein the rice male sterile line is a cytoplasmic male sterile line selected from the group consisting of a rice cytoplasmic male sterile line CMS-Koshihikari eichi 2go (*Oryza sativa* L. cultivar Koshihikari eichi 2go), a rice cytoplasmic male sterile line CMS-Koshihikari eichi 3go, a rice cytoplasmic male sterile line CMS-Koshihikari eichi 4go, a rice cytoplasmic male sterile line CMS-Koshihikari kazusa 1 go, a rice cytoplasmic male sterile line CMS-Koshihikari kazusa 2go, and a rice cytoplasmic male sterile line CMS-Koshihikari kazusa 3go, (3) A rice F1 seed which is obtained by the method for producing a rice F1 seed of (1) or (2), (4) A rice male sterile line containing one or more genes selected from the group consisting of the sd1 gene derived from *Oryza sativa* L. cultivar Habataki, the Gn1 gene derived from *Oryza sativa* L. cultivar Habataki, and the hd1 gene derived from *Oryza sativa* L. cultivar Habataki.

(5) A rice cytoplasmic male sterile line CMS-Koshihikari eichi 2go (*Oryza sativa* L. cultivar Koshihikari eichi 2go), (6) A rice cytoplasmic male sterile line CMS-Koshihikari eichi 3go (*Oryza sativa* L. cultivar Koshihikari eichi 3go), (7) A rice cytoplasmic male sterile line CMS-Koshihikari eichi 4go (*Oryza sativa* L. cultivar Koshihikari eichi 4go), (8) A rice cytoplasmic male sterile line CMS-Koshihikari kazusa 1go (*Oryza sativa* L. cultivar Koshihikari kazusa 1go), (9) A rice cytoplasmic male sterile line CMS-Koshihikari kazusa 2go (*Oryza sativa* L. cultivar Koshihikari kazusa 2go),

(10) A rice cytoplasmic male sterile line CMS-Koshihikari kazusa 3go (*Oryza sativa* L. cultivar Koshihikari kazusa 3go).

Advantage of the Invention

The method for producing a rice F1 seed in accordance with the present invention employs a rice male sterile line with improvement of a specific characteristic as a seed parent and is therefore capable of producing an F1 hybrid seed having such a characteristic. In particular, in the present invention, when a rice male sterile line containing the sd1 gene derived from *Oryza sativa* L. cultivar Habataki is used as a seed parent, an F1 hybrid having a significantly short culm length and an improved lodging resistance may be created, as compared to when a male sterile line of *Oryza sativa* L. cultivar Koshihikari is used as a seed parent. Further, when a rice male sterile line containing the Gn1 gene derived from *Oryza sativa* L. cultivar Habataki is used as a seed parent, an F1 hybrid having a higher grain density may be created, as compared to when a male sterile line of *Oryza saliva* L. cultivar Koshihikari is used as a seed parent. Further, when a rice male sterile line containing the hd1 gene derived from *Oryza sativa* L. cultivar Habataki is used as a seed parent, an F1 hybrid converted to have earlier growth may be created, as compared to when a male sterile line of *Oryza saliva* L. cultivar Koshihikari is used as a seed parent. Further, when a rice male sterile line having semi-waxiness is used as a seed parent, an F1 hybrid having a superior taste quality may be created, as compared to when a male sterile line of *Oryza sativa* L. cultivar Koshihikari is used as a seed parent.

DETAILED DESCRIPTION OF THE INVENTION

Figure 1:
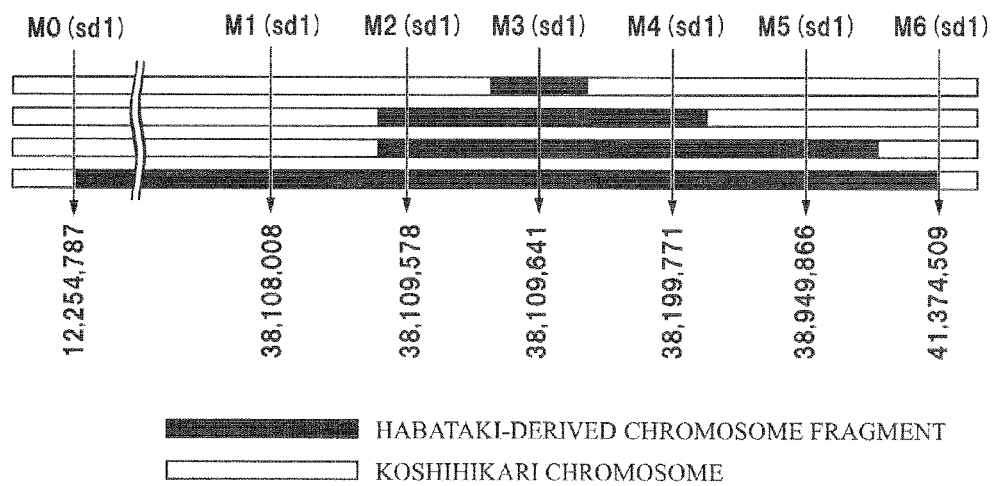
FIG. 1 is a view showing a DNA marker (SNP) of the vicinity in which the sd1 gene in the chromosome 1 of rice is encoded.

In the present invention, the term "near-isogenic line" means a line in which only a part of a chromosome of an original cultivar is substituted with a chromosome fragment derived from a foreign cultivar. The foreign cultivar is not particularly limited as long as it is a cultivar other than an original cultivar, and may be a cultivar of a plant which is the same species as that of an original cultivar, may be a cultivar of a plant which is a different species from that of an original cultivar, and may be a cultivar other than a plant such as an animal. In the present invention, the term "cultivar" means a population which is the same species of a plant, but can be clearly discriminated from other species in the same species in a certain characteristic, due to different genetic constitution.

The DNA markers in the present invention are not particularly limited as long as they can discriminate between a chromosome derived from an original cultivar and a chromosome derived from a foreign cultivar, that is, they can detect a difference in a DNA sequence on a chromosome between the original cultivar and the foreign cultivar, and a DNA marker which is conventionally used in the gene analysis field may be used. These DNA markers may be, for example, a marker which can detect gene polymorphism such as SNP (Single Nucleotide Polymorphism) or a difference in the repetition number of SSR (Simple Sequence Repeats), or may be a RFLP (Restriction Fragment Length Polymorphism) marker. Discrimination between an allele derived from the original cultivar and an allele derived from the foreign cultivar using these DNA markers may be carried out by a conventional method. For example, PCR is carried out as follows: employing DNA extracted from each individual as a template; and using primers which are capable of specifically hybridizing with particular SNP and SSR. Then, by detecting the presence or the absence of the PCR product using an electrophoresis method or the like, each polymorphism may be discriminated. Alternatively, by detecting a pattern of a DNA fragment using an electrophoresis method or the like after DNA extracted from each individual is treated with a restriction enzyme, each polymorphism may be discriminated. Primers which are capable of specifically hybridizing with particular SNP or SSR may be designed by a conventional method using a primer design tool which is generally used, depending on a nucleotide sequence of SNP and SSR. In addition, designed primers may be synthesized using any method well-known in the art.

A known DNA marker may be optionally used as the DNA marker. Alternatively, the DNA marker may be a newly prepared DNA marker. For example, when a known DNA marker regarding rice is used, SNP markers disclosed in the pamphlet of International Publication No. WO 2003/070934, and DNA markers published in Rice Genome Research Program may be used.

Genetic information of each cultivar is available, for example, from the National Center for Biotechnology Information (NCBI) or the DNA Data Bank of Japan (DDBJ), which are international nucleotide sequence databases. Particularly, genetic information of each cultivar of rice is available in Knowledge-based Oryza Molecular Biological Encyclopedia.

In the present invention and the present specification, "the $X^{th}$ base of a chromosome of *Oryza sativa* L. cultivar Nipponbare" is a region which is determined based on the base sequence of genomic DNA of *Oryza sativa* L. cultivar Nipponbare (version 2) published on the website for The Institute for Genomic Research.

In the present invention and the present specification, the term "region corresponding to a region from the $X^{th}$ base to the $Y^{th}$ base of a chromosome of *Oryza sativa* L. cultivar Nipponbare" refers to a region in a chromosome of a rice individual, which exhibits a high homology with the region from the $X^{th}$ base to the $Y^{th}$ base of a chromosome of *Oryza sativa* L. cultivar Nipponbare, and may be determined in such a manner that the base sequence of a known genomic DNA of *Oryza sativa* L. cultivar Nipponbare and the base sequence of a genomic DNA of the rice individual are aligned to make the highest homology therebetween. The term "SNP corresponding to SNP of *Oryza sativa* L. cultivar Nipponbare" in a rice individual other than *Oryza sativa* L. cultivar Nipponbare refers to, in a region containing the SNP, a base at the position corresponding to the SNP when the base sequence of a known genomic DNA of *Oryza saliva* L. cultivar Nipponbare and the base sequence of a genomic DNA of the rice individual are aligned to make the highest homology therebetween.

The method for producing a rice F1 seed in accordance with the present invention includes crossing a male sterile line of *Oryza sativa* L. cultivar Koshihikari having an improved specific characteristic as a seed parent with a rice fertility restorer line as a pollen parent, and collecting the first filial generation seed (F1 seed) from the post-crossing seed parent.

First, a rice male sterile line used in the present invention will be described. The rice male sterile line used in the present invention is a male sterile line of a near-isogenic line in which a specific characteristic is improved through the substitution of a part of a chromosome of *Oryza sativa* L. cultivar Koshihikari with a chromosome fragment derived from a foreign cultivar or by mutagenesis.

The male sterile line of a near-isogenic line may be created by a conventional method. For example, a Koshihikari cytoplasmic male sterile line having the same characteristic as *Oryza saliva* L. cultivar Koshihikari except that it is of cytoplasmic male sterility is crossed with a near-isogenic line of *Oryza sativa* L. cultivar Koshihikari in which a desired region is substituted with a chromosome fragment derived from foreign cultivar or a desired mutation is made, and the resulting F1 hybrid is subjected to continuous backcrossing using a near-isogenic line of the *Oryza sativa* L. cultivar Koshihikari as a pollen parent, whereby a rice cytoplasmic male sterile line having the same characteristic as a near-isogenic line of the *Oryza sativa* L. cultivar Koshihikari except that it is of cytoplasmic male sterility may be obtained. In addition, a Koshihikari cytoplasmic male sterile line may be created, for example, by crossing an *Oryza sativa* L. cultivar Koshihikari and a rice cytoplasmic male sterile line, and repeatedly backcrossing the resulting F1 hybrid, using an *Oryza sativa* L. cultivar Koshihikari as a pollen parent. The rice cytoplasmic male sterile line is not particularly limited as long as it is a gramineous cultivar exhibiting cytoplasmic male sterility. Examples of the rice cytoplasmic male sterile line include *Oryza sativa* L. cultivar CHINSURAH BORO 2 which is of BT-type cytoplasmic male sterility, *Oryza sativa* L. cultivar Male sterile wild rice which is of WA-type cytoplasmic male sterility, *Oryza sativa* L. cultivar Gambiaca which is of GA-type cytoplasmic male sterility, and *Oryza sativa* L. cultivar Dissi which is of Di-type cytoplasmic male sterility.

Further, the male sterile line of a near-isogenic line may be an environmental condition-dependent male sterile line due to a mutant gene leading to sterility under specific environmental conditions. Examples of the environmental condition-dependent male sterile line include a photoperiod-sensitive genic male sterile (PGMS) line using a PMS1 gene or PMS2 gene leading to male sterility under long-day conditions, and a thermo-sensitive genic male sterile (TGMS) line using a TMS1 gene or TMS2 gene leading to male sterility under high temperature conditions. A rice male sterile line having the same characteristic as a near-isogenic line of the *Oryza saliva* L. cultivar Koshihikari except that it exhibits environmental condition-dependent male sterility due to the mutant gene may be obtained by crossing a near-isogenic line of *Oryza sativa* L. cultivar Koshihikari with an environmental condition-dependent male sterile line having such a mutant gene, and subjecting the resulting F1 hybrid to continuous backcrossing using the near-isogenic line of *Oryza sativa* L. cultivar Koshihikari as a pollen parent.

First, a near-isogenic line of *Oryza sativa* L. cultivar Koshihikari in which a chromosome of *Oryza saliva* L. cultivar Koshihikari has been partially substituted with a chromosome fragment derived from a foreign cultivar will be described as a seed parent.

The foreign cultivar-derived chromosome fragment being inserted in a near-isogenic line of *Oryza sativa* L. cultivar Koshihikari is not particularly limited as long as insertion of the chromosome fragment results in more improvement of a specific characteristic than *Oryza sativa* L. cultivar Koshihikari. For example, it is sufficient that the foreign cultivar-derived chromosome fragment to be inserted contains a region encoding a gene directly contributing to desired characteristic improvement (causative gene). The foreign cultivar-derived chromosome fragment may be a region containing only a causative gene, or a region containing the causative gene and other genes (for example, a region consisting of 14.6 Mbp to 29.2 Mbp in length).

In the present invention and the present specification, the term ""Y" gene derived from *Oryza sativa* L. cultivar "X"" is intended to encompass a "Y" gene derived from *Oryza saliva* L. cultivar "X" itself (that is, a "Y" gene present in a chromosome of *Oryza sativa* L. cultivar "X"), as well as a "Y" gene derived from *Oryza sativa* L. cultivar having a "Y" gene substantially identical to that of *Oryza sativa* L. cultivar "X". This is because the same effect as in the present invention is exhibited even when, in place of a "Y" gene derived from *Oryza sativa* L. cultivar "X", a "Y" gene derived from *Oryza sativa* L. cultivar other than *Oryza sativa* L. cultivar "X", which is substantially identical to a "Y" gene derived from *Oryza sativa* L. cultivar "X", is incorporated into a chromosome. Here, the "Y" gene substantially identical to a "Y" gene derived from *Oryza sativa* L. cultivar "X" refers to a "Y" gene which is derived from *Oryza sativa* L. cultivar other than *Oryza sativa* L. cultivar "X" and has a function virtually equivalent to that of a "Y" gene derived from *Oryza sativa* L. cultivar "X". Specific examples thereof include an *Oryza sativa* L. cultivar, which is a posterity cultivar of *Oryza sativa* L. cultivar "X" and has inherited alleles of a "Y" gene-containing region from *Oryza sativa* L. cultivar "X", an *Oryza sativa* L. cultivar, which corresponds to an ancestor of *Oryza sativa* L. cultivar "X" and has alleles of a "Y" gene-containing region in common in *Oryza sativa* L. cultivar "X", and an *Oryza sativa* L. cultivar into which a chromosome fragment of a "Y" gene-containing region contained in *Oryza sativa* L. cultivar having a "Y" gene substantially identical to that of these *Oryza sativa* L. cultivar "X" has been incorporated.

That is, in the present invention and the present specification, unless otherwise specifically indicated, the term "sd1 gene derived from *Oryza sativa* L. cultivar Habataki" is intended to encompass an sd1 gene derived from *Oryza sativa* L. cultivar Habataki itself as well as an sd1 gene substantially identical to that gene, for example, an sd1 gene derived from *Oryza saliva* L. cultivar such as *Oryza sativa* L. cultivar Dee-Geo-Woo-Gen, *Oryza sativa* L. cultivar IR8, *Oryza sativa* L. cultivar Kinuhikari, *Oryza sativa* L. cultivar Yumehitachi, *Oryza saliva* L. cultivar Koshihikari eichi 4go, *Oryza sativa* L. cultivar Koshihikari kazusa 2go, *Oryza sativa* L. cultivar Koshihikari kazusa 3go, or *Oryza sativa* L. cultivar Koshihikari kazusa 4go.

Similarly, in the present invention and the present specification, unless otherwise specifically indicated, the term "Gn1 gene derived from *Oryza sativa* L. cultivar Habataki" is intended to encompass a Gn1 gene derived from *Oryza sativa* L. cultivar Habataki itself as well as a Gn1 gene substantially identical to that gene, for example, a Gn1 gene derived from *Oryza sativa* L. cultivar such as *Oryza sativa* L. cultivar Koshihikari eichi 2go, *Oryza sativa* L. cultivar Koshihikari kazusa 2go, *Oryza sativa* L. cultivar Koshihikari kazusa 3go, or *Oryza sativa* L. cultivar Koshihikari kazusa 4go.

Similarly, in the present invention and the present specification, unless otherwise specifically indicated, the term "hd1 gene derived from *Oryza sativa* L. cultivar Habataki" is intended to encompass an hd1 gene derived from *Oryza sativa* L. cultivar Habataki itself as well as an hd1 gene substantially identical to that gene, for example, an hd1 gene derived from *Oryza sativa* L. cultivar such as *Oryza sativa* L. cultivar Koshihikari eichi 3go, *Oryza sativa* L. cultivar Koshihikari kazusa 1go, *Oryza sativa* L. cultivar Koshihikari kazusa 2go, or *Oryza sativa* L. cultivar Koshihikari kazusa 4go.

In the present invention, a rice male sterile line containing one or more genes selected from the group consisting of the sd1 gene derived from *Oryza saliva* L. cultivar Habataki, the Gn1 gene derived from *Oryza sativa* L. cultivar Habataki, and the hd1 gene derived from *Oryza sativa* L. cultivar Habataki is employed as a seed parent. Among these three genes, a male sterile line containing an appropriate combination of two genes, or a male sterile line containing all of three genes may also be used as a seed parent.

The rice male sterile line containing one or more genes selected from the group consisting of the sd1 gene derived from *Oryza sativa* L. cultivar Habataki, the Gn1 gene derived from *Oryza sativa* L. cultivar Habataki, and the hd1 gene derived from *Oryza sativa* L. cultivar Habataki may be created from a near-isogenic line of *Oryza sativa* L. cultivar Koshihikari containing one or more genes selected from the group consisting of the sd1 gene derived from *Oryza sativa* L. cultivar Habataki, the Gn1 gene derived from *Oryza saliva* L. cultivar Habataki, and the hd1 gene derived from *Oryza sativa* L. cultivar Habataki, and a Koshihikari male sterile line, according to the above-mentioned method. The near-isogenic line of *Oryza saliva* L. cultivar Koshihikari containing one or more genes selected from the group consisting of the sd1 gene derived from *Oryza sativa* L. cultivar Habataki, the Gn1 gene derived from *Oryza sativa* L. cultivar Habataki, and the hd1 gene derived from *Oryza sativa* L. cultivar Habataki may be created, for example, by using an appropriate DNA marker, according to the method disclosed in Patent Document 3 and Patent Document 4 or other methods. Further, the near-isogenic line of *Oryza sativa* L. cultivar Koshihikari as a seed parent used in the present invention may be a newly created line or may be a conventional line.

In the near-isogenic line of *Oryza sativa* L. cultivar Koshihikari containing the sd1 gene derived from *Oryza sativa* L. cultivar Habataki (Habataki-derived sd1-containing near-isogenic line), the region in which the sd1 gene in a chromosome of *Oryza sativa* L. cultivar Koshihikari is encoded has been substituted with a chromosome fragment containing a region encoding the sd1 gene derived from *Oryza sativa* L. cultivar Habataki. The Habataki-derived chromosome fragment contained in the Habataki-derived sd1-containing near-isogenic line is not particularly limited as long as it contains a region in which the sd1 gene is encoded, and may contain only the region in which the sd1 gene is encoded, and a gene present in the proximity of the sd1 gene, together with the sd1 gene, may also be inserted into *Oryza sativa* L. cultivar Koshihikari. FIG. 1 shows a DNA marker (SNP) of approximately 38.11 Mbp in which the sd1 gene in the chromosome 1 of rice is encoded. A length of the Habataki-derived chromosome fragment may be determined by using a DNA marker. For example, as shown in FIG. 1, in the Habataki-derived sd1-containing near-isogenic line, an end on an upstream side of the inserted Habataki-derived chromosome fragment may be present between polymorphism dependent on the base sequence at the position of 38,109,578 in the chromosome 1 of *Oryza sativa* L. cultivar Nipponbare (when performing PCR, the PCR product can be obtained from *Oryza saliva* L. cultivar Koshihikari, whereas the PCR product cannot be obtained from *Oryza sativa* L. cultivar Habataki) (hereinafter, referred to as "G2003") and polymorphism dependent on the base sequence at the position of 38,109,641 in the chromosome 1 of *Oryza sativa* L. cultivar Nipponbare (when performing PCR, the PCR product can be obtained from *Oryza sativa* L. cultivar Koshihikari, whereas the PCR product cannot be obtained from *Oryza saliva* L. cultivar Habataki) (hereinafter, referred to as "G2002"), and an end on a downstream side of the Habataki-derived chromosome fragment may be present between G2003 and SNP corresponding to SNP at the position of 38,199,771 in the chromosome 1 of *Oryza sativa* L. cultivar Nipponbare (G in *Oryza sativa* L. cultivar Koshihikari, and T in *Oryza sativa* L. cultivar Habataki) (hereinafter, referred to as "SP-462") (first step in FIG. 1). Alternatively, an end on an upstream side of the Habataki-derived chromosome fragment may be present between SNP corresponding to SNP at the position of 38,108,008 in the chromosome 1 of *Oryza sativa* L. cultivar Nipponbare (G in *Oryza saliva* L. cultivar Koshihikari, and C in *Oryza sativa* L. cultivar Habataki) (hereinafter, referred to as "SP-4009") and G2003, and an end on a downstream side of the Habataki-derived chromosome fragment may be present between SP-462 and SNP corresponding to SNP at the position of 38,949,866 in the chromosome 1 of *Oryza saliva* L. cultivar Nipponbare (T in *Oryza saliva* L. cultivar Koshihikari, and C in *Oryza saliva* L. cultivar Habataki) (hereinafter, referred to as "SP-1259") (second step in FIG. 1). An end on an upstream side of the Habataki-derived chromosome fragment may be present between SP-4009 and G2003, and an end on a downstream side of the Habataki-derived chromosome fragment may be present between SP-1259 and SNP corresponding to SNP at the position of 41,374,509 in the chromosome 1 of *Oryza sativa* L. cultivar Nipponbare (A in *Oryza sativa* L. cultivar Koshihikari, and G in *Oryza sativa* L. cultivar Habataki) (hereinafter, referred to as "SP-477") (third step in FIG. 1).

Figure 2:
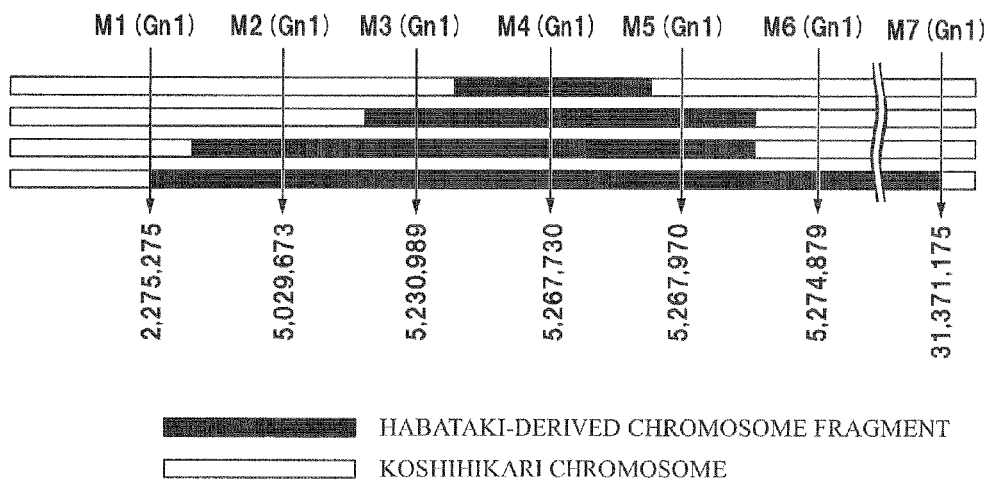
FIG. 2 is a view showing a DNA marker (SNP) of the vicinity in which the Gn1 gene in the chromosome 1 of rice is encoded.

Further, a longer region, containing a region encoding the sd1 gene derived from *Oryza sativa* L. cultivar Habataki, may be substituted with the Habataki-derived chromosome fragment. For example, the region containing a region of approximately 29.1 Mbp ranging from SNP corresponding to SNP at the position of 12,254,787 in the chromosome 1 of *Oryza sativa* L. cultivar Nipponbare (G in *Oryza sativa* L. cultivar Koshihikari, and C in *Oryza sativa* L. cultivar Habataki) (hereinafter, referred to as "SP-2058") to SP-477 may be substituted with the Habataki-derived chromosome fragment (fourth step in FIG. 1). Base sequences of individual DNA markers and primers usable in discrimination are shown in Table 1.

into *Oryza sativa* L. cultivar Koshihikari. FIG. 2 shows a DNA marker (SNP) of approximately 5.267 Mbp in which the Gn1 gene in the chromosome 1 of rice is encoded. A length of the Habataki-derived chromosome fragment may be determined by using a DNA marker. For example, as shown in FIG. 2, in the Habataki-derived Gn1-containing near-isogenic line, an end on an upstream side of the inserted Habataki-derived chromosome fragment may be present between SNP corresponding to SNP at the position of 5,230,989 in the chromosome 1 of *Oryza sativa* L. cultivar Nipponbare (T in *Oryza sativa* L. cultivar Koshihikari, and A in *Oryza saliva* L. cultivar Habataki) (hereinafter, referred to as "SP-170") and SNP corresponding to SNP at the

TABLE 1

| Marker | | Position in the chromosome 1 | Type | Sequence | SEQ ID NO: |
|---|---|---|---|---|---|
| M0(sd1) | SP-2058 | 12,254,787 | Gc | Upper Seq: TGCTACAACTGTACACACTG | 1 |
| | | | | Lower Seq: GCTCGAAGACACATTGGTTC | 2 |
| | | | | SNP primer: AGTAGAAAAACCAACACCTT | 3 |
| M1(sd1) | SP-4009 | 28,108,008 | Gc | Upper Seq: CCGTTATGTGCCTGTATGG | 4 |
| | | | | Lower Seq: TGTTGCAGGAAGGTGACAGG | 5 |
| | | | | SNP primer: TTGGAAGGAACATCTAGCACA | 6 |
| M2(sd1) | G2003 | 38,109,578 | PCR | Upper Seq: CACAGCGCTCACTTCTCA | 7 |
| | | | | Lower Seq: TGCAATGTCGTCCACCATCG | 8 |
| M3(sd1) | G2002 | 38,109,641 | PCR | Upper Seq: CACAGCGCTCACTTCTCA | 9 |
| | | | | Lower Seq: ATGATCGTCAGCGACAGCT | 10 |
| M4(sd1) | SP-462 | 38,199,771 | Gt | Upper Seq: AACTCCAGCGTGCTAAGC | 11 |
| | | | | Lower Seq: GCATTGCATGCAGGATCG | 12 |
| | | | | SNP primer: AGAGCCCTTCACTTTCAGC | 13 |
| M5(sd1) | SP-1259 | 38,949,866 | Tc | Upper Seq: AAGGCTGATGAGCACTGC | 14 |
| | | | | Lower Seq: GGCATTGTGGAAGCTCTTC | 15 |
| | | | | SNP primer: TCTCCTTTCGGAGTCCC | 16 |
| M6(sd1) | SP-477 | 41,374,509 | Ag | Upper Seq: GCTATGTTGAACAAGTTCGCTG | 17 |
| | | | | Lower Seq: CATCGTGGACAGCAATCTTG | 18 |
| | | | | SNP primer: GTATAGTTAGTCATGTGCC | 19 |

An F1 hybrid obtained by using the rice male sterile line containing the Habataki-derived sd1 gene as a seed parent contains the Habataki-derived sd1 gene and therefore exhibits a significantly low culm length and improved lodging resistance, as compared to an F1 hybrid obtained by using a Koshihikari male sterile line as a seed parent. For this reason, in the method for producing a rice F1 seed in accordance with the present invention, by using a rice male sterile line containing the Habataki-derived sd1 gene, seeds of an F1 hybrid with improved lodging resistance can be efficiently produced, and efficiency of a combinatorial test for rearing an F1 hybrid can be improved.

In the near-isogenic line of *Oryza sativa* L. cultivar Koshihikari containing the Gn1 gene derived from *Oryza sativa* L. cultivar Habataki (Habataki-derived Gn1-containing near-isogenic line), the region in which the Gn1 gene in a chromosome of *Oryza sativa* L. cultivar Koshihikari is encoded has been substituted with a chromosome fragment containing a region encoding the Gn1 gene derived from *Oryza sativa* L. cultivar Habataki. The Habataki-derived chromosome fragment contained in the Habataki-derived Gn1-containing near-isogenic line is not particularly limited as long as it contains a region in which the Gn1 gene is encoded, and may contain only the region in which the Gn1 gene is encoded, and a gene present in the proximity of the Gn1 gene, together with the Gn1 gene, may also be inserted position of 5,267,730 in the chromosome 1 of *Oryza sativa* L. cultivar Nipponbare (A in *Oryza sativa* L. cultivar Koshihikari, and C in *Oryza sativa* L. cultivar Habataki) (hereinafter, referred to as "SP-4028"), and an end on a downstream side of the Habataki-derived chromosome fragment may be present between SP-4028 and SNP corresponding to SNP at the position of 5,267,970 in the chromosome 1 of *Oryza sativa* L. cultivar Nipponbare (G in *Oryza sativa* L. cultivar Koshihikari, and C in *Oryza saliva* L. cultivar Habataki) (hereinafter, referred to as "SP-4038") (first step in FIG. 2). Alternatively, an end on an upstream side of the Habataki-derived chromosome fragment may be present between SNP corresponding to SNP at the position of 5,029,673 in the chromosome 1 of *Oryza sativa* L. cultivar Nipponbare (T in *Oryza sativa* L. cultivar Koshihikari, and G in *Oryza sativa* L. cultivar Habataki) (hereinafter, referred to as "SP-2032") and SP-170, and an end on a downstream side of the Habataki-derived chromosome fragment may be present between SP-4038 and SNP corresponding to SNP at the position of 5,274,879 in the chromosome 1 of *Oryza saliva* L. cultivar Nipponbare (A in *Oryza sativa* L. cultivar Koshihikari, and T in *Oryza saliva* L. cultivar Habataki) (hereinafter, referred to as "SP-4030") (second step in FIG. 2). An end on an upstream side of the Habataki-derived chromosome fragment may be present between SNP corresponding to SNP at the position of 2,275,275 in the chromosome 1 of Oryza saliva L. cultivar Nipponbare (G in Oryza saliva L. cultivar Koshihikari, and C in Oryza saliva L. cultivar Habataki) (hereinafter, referred to as "SP-158") and SP-2032, and an end on a downstream side of the Habataki-derived chromosome fragment may be present between SP-4038 and SP-4030 (third step in FIG. 2). Further, a longer region, containing a region encoding the Gn1 gene derived from Oryza saliva L. cultivar Habataki may be substituted with the Habataki-derived chromosome fragment. For example, the region containing a region of approximately 29.1 Mbp ranging from SP-158 to SNP corresponding to SNP at the position of 31,371,175 in the chromosome 1 of Oryza saliva L. cultivar Nipponbare (G in Oryza saliva L. cultivar Koshihikari, and A in Oryza saliva L. cultivar Habataki) (hereinafter, referred to as "SP-262") may be substituted with the Habataki-derived chromosome fragment (fourth step in FIG. 2). Base sequences of individual DNA markers and primers usable in discrimination are shown in Table 2.

Figure 3:
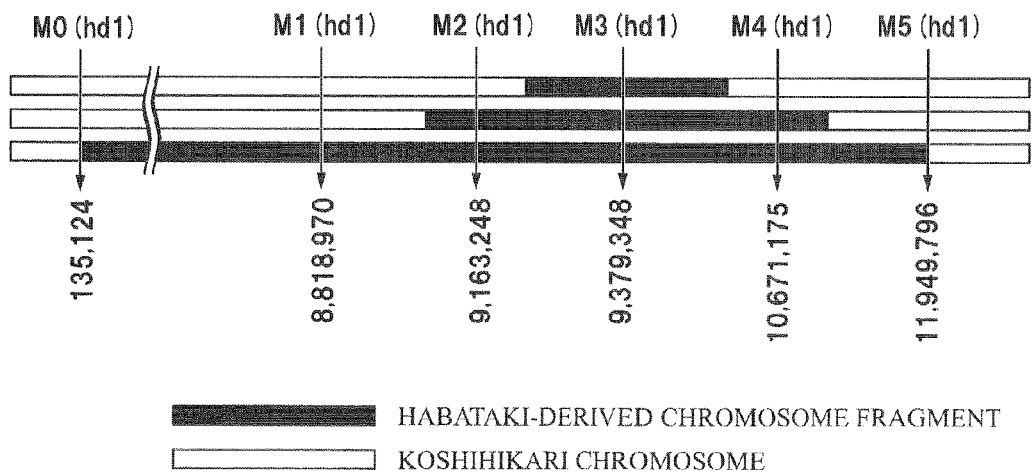
FIG. 3 is a view showing a DNA marker (SNP) of the vicinity in which the hd1 gene in the chromosome 6 of rice is encoded.

Oryza sativa L. cultivar Habataki. The Habataki-derived chromosome fragment contained in the Habataki-derived hd1-containing near-isogenic line is not particularly limited as long as it contains a region in which the hd1 gene is encoded, and may contain only the region in which the hd1 gene is encoded, and a gene present in the proximity of the hd1 gene, together with the hd1 gene, may also be inserted into Oryza sativa L. cultivar Koshihikari. FIG. 3 shows a DNA marker (SNP) of approximately 9.38 Mbp in which the hd1 gene in the chromosome 1 of rice is encoded. A length of the Habataki-derived chromosome fragment may be determined by using a DNA marker. For example, as shown in FIG. 3, in the Habataki-derived hd1-containing near-isogenic line, an end on an upstream side of the inserted Habataki-derived chromosome fragment may be present between SNP corresponding to SNP at the position of 9,163,248 in the chromosome 6 of Oryza sativa L. cultivar Nipponbare (C in Oryza sativa L. cultivar Koshihikari, and A in Oryza sativa L. cultivar Habataki) (hereinafter, referred

TABLE 2

| Marker | Position in the chromosome 1 | Type | Sequence | | SEQ ID NO: |
|---|---|---|---|---|---|
| M1(Gn1) | SP-156 | 2,275,275 | Gc | Upper Seq: GGAATTCAGAGACAACATGG | 20 |
| | | | | Lower Seq: GCTTCAGTGTTGTGTGATTCTG | 21 |
| | | | | SNP primer: AACGAGTTCTACAATGCTGC | 22 |
| M2(Gn1) | SP-2032 | 5,029,673 | Tg | Upper Seq: CATTGAGTCCATTTCCTCTGC | 23 |
| | | | | Lower Seq: GCAGCTCCAAGAATGACTAC | 24 |
| | | | | SNP primer: ATTGGTGCTAGAGCAACTAC | 25 |
| M3(Gn1) | 170 | 5,230,989 | Ta | Upper Seq: GTGAGACATAGACTATCCAC | 26 |
| | | | | Lower Seq: ACGCGTACGCCACATAGAC | 27 |
| | | | | SNP primer: AGGGTGAGGAATGTCCGGT | 28 |
| M4(Gn1) | SP-4028 | 5,267,730 | Ac | Upper Seq: GCAGTACCTGCCTTACTACG | 29 |
| | | | | Lower Seq: CATTTCATGCGAGTGGTGAC | 30 |
| | | | | SNP primer: TGCACGAATCTTGGCCAGAG | 31 |
| M5(Gn1) | SP-4038 | 5,267,970 | Gc | Upper Seq: CTTAAACTCAACTTGCACAAGTAG | 32 |
| | | | | Lower Seq: ACTGCCGACATGTTACTGTC | 33 |
| | | | | SNP primer: GTCCCACCTGAAACATATCCA | 34 |
| M6(Gn1) | SP-4030 | 5,274,879 | At | Upper Seq: TCTTTGATTCTTTGGTCGATCG | 35 |
| | | | | Lower Seq: GCGTACGAGAGCTATAGAGC | 36 |
| | | | | SNP primer: ATGGATCCGTGGATCGATCG | 37 |
| M7(Gn1) | SP-262 | 31,371,175 | Ga | Upper Seq: GCAGCAGGACAAAGGCTAAC | 38 |
| | | | | Lower Seq: ACCCTTCTTCAAGCTCCATC | 39 |
| | | | | SNP primer: TCACAACCGGACCAGATGAC | 40 |

An F1 hybrid obtained by using the rice male sterile line containing the Habataki-derived Gn1 gene as a seed parent contains the Habataki-derived Gn1 gene and therefore exhibits an improved grain density, as compared to an F1 hybrid obtained by using a Koshihikari male sterile line as a seed parent. For this reason, in the method for producing a rice F1 seed in accordance with the present invention, by using a rice male sterile line containing the Habataki-derived Gn1 gene, seeds of an F1 hybrid with improved grain density can be efficiently produced, and efficiency of a combinatorial test for rearing an F1 hybrid can be improved.

In the near-isogenic line of Oryza sativa L. cultivar Koshihikari containing the hd1 gene derived from Oryza sativa L. cultivar Habataki (Habataki-derived hd1-containing near-isogenic line), the region in which the hd1 gene in a chromosome of Oryza sativa L. cultivar Koshihikari is encoded has been substituted with a chromosome fragment containing a region encoding the hd1 gene derived from to as "SP-586") and SNP corresponding to SNP at the position of 9,379,348 in the chromosome 6 of Oryza sativa L. cultivar Nipponbare (C in Oryza sativa L. cultivar Koshihikari, and G in Oryza sativa L. cultivar Habataki) (hereinafter, referred to as "SP-2254"), and an end on a downstream side of the Habataki-derived chromosome fragment may be present between SP-2254 and SNP corresponding to SNP at the position of 10,671,175 in the chromosome 6 of Oryza sativa L. cultivar Nipponbare (T in Oryza sativa L. cultivar Koshihikari, and C in Oryza sativa L. cultivar Habataki) (hereinafter, referred to as "SP-1603") (top in FIG. 3). Further, an end on an upstream side of the Habataki-derived chromosome fragment may be present between SNP corresponding to SNP at the position of 8,818,970 in the chromosome 6 of Oryza saliva L. cultivar Nipponbare (C in Oryza sativa L. cultivar Koshihikari, and T in Oryza sativa L. cultivar Habataki) (hereinafter, referred to as "SP-2513") and SP-586, and an end on a downstream side of the Habataki-derived chromosome fragment may be present between SP-1603 and SNP corresponding to SNP at the position of 11,949,796 in the chromosome 6 of *Oryza sativa* L. cultivar Nipponbare (T in *Oryza sativa* L. cultivar Koshihikari, and C in *Oryza sativa* L. cultivar Habataki) (hereinafter, referred to as "SP-604") (middle in FIG. 3). Further, a longer region, containing a region encoding the hd1 gene derived from *Oryza sativa* L. cultivar Habataki may be substituted with the Habataki-derived chromosome fragment. For example, the region containing a region of approximately 28.9 Mbp ranging from SNP corresponding to SNP at the position of 135,124 in the chromosome 6 of *Oryza sativa* L. cultivar Nipponbare (A in *Oryza sativa* L. cultivar Koshihikari, and G in *Oryza sativa* L. cultivar Habataki) (hereinafter, referred to as "SP-2229") to SNP corresponding to SNP at the position of 29,016,207 in the chromosome 6 of *Oryza sativa* L. cultivar Nipponbare (G in *Oryza sativa* L. cultivar Koshihikari, and T in *Oryza sativa* L. cultivar Habataki) (hereinafter, referred to as "SP-1635") may be substituted with the Habataki-derived chromosome fragment (bottom in FIG. 3). Base sequences of individual DNA markers and primers usable in discrimination are shown in Table 3.

gene and the hd1 gene have been substituted with genes derived from Habataki may be obtained by crossing near-isogenic lines in which different kinds of genes have been substituted with genes derived from Habataki, and selecting a homo-individual where a gene derived from the foreign gene introduced into a chromosome of *Oryza sativa* L. cultivar Koshihikari has been introduced into homologous chromosomes of both parties, using a DNA marker, from the F2 hybrid obtained by self-mating the resulting F1 hybrid. For example, the near-isogenic line of *Oryza sativa* L. cultivar Koshihikari in which the sd1 gene and Gn1 gene have been substituted with genes derived from Habataki (Habataki-derived sd1/Habataki-derived Gn1-containing near-isogenic line) may be created by crossing a near-isogenic line containing the Habataki-derived sd1 and a near-isogenic line containing the Habataki-derived Gn1, and selecting an individual in which all of the region in which the sd1 gene is encoded and the region in which the Gn1 gene is encoded are a region derived from Habataki, in homologous chromosomes of both parties, using a DNA marker as an indicator, from the second filial generation (F2 hybrid) obtained by self-mating the resulting F1 hybrid. In the same manner, the near-isogenic line of *Oryza sativa* L.

TABLE 3

| Marker | | Position in the chromosome 6 | Type | Sequence | SEQ ID NO: |
|---|---|---|---|---|---|
| M0(hd1) | SP-2229 | 135,124 | Ag | Upper Seq: CAATCTGGGATTCTGGATCAG | 41 |
| | | | | Lower Seq: AGCTCAGTATCACGGACTTG | 42 |
| | | | | SNP primer: GTCTCTTTTAACACACCTTAC | 43 |
| M1(hd1) | SP-2513 | 8,818,970 | Ct | Upper Seq: GCGAAAAGATGAGGATGTACAC | 44 |
| | | | | Lower Seq: CCGTAGGCCTTTGTCAAGTG | 45 |
| | | | | SNP primer: CTTTAATGGTGGCTTATGTC | 46 |
| M2(hd1) | SP-586 | 9,163,248 | Ca | Upper Seq: GCTAGGACAAGCTTATTTCAGC | 47 |
| | | | | Lower Seq: TCACGCCGATCAAGAACG | 48 |
| | | | | SNP primer: CATAATTTATCGCCATTTTCGCAT | 49 |
| M3(hd1) | SP-2254 | 9,379,348 | Cg | Upper Seq: AGGCCCTTGTACTGGTAC | 50 |
| | | | | Lower Seq: GTACACAATAGTTGGTGCACC | 51 |
| | | | | SNP primer: CATGATAAGGTACTCCTGG | 52 |
| M4(hd1) | SP-1603 | 10,671,175 | Tc | Upper Seq: CCTAGTCCCTAAAGATCTCATG | 53 |
| | | | | Lower Seq: GATAGACATGACGGAGAAGTG | 54 |
| | | | | SNP primer: GGGTGGTGTTATCTCTAGT | 55 |
| M5(hd1) | SP-604 | 11,949,796 | Tc | Upper Seq: GCGCAAATTCCTTCAGTCAC | 56 |
| | | | | Lower Seq: CAGTTTCAGGTGGAAGACC | 57 |
| | | | | SNP primer: CAAGTTTCTTCCTCTCATTTTC | 58 |
| M6(hd1) | SP-1635 | 29,016,207 | Gt | Upper Seq: TAGGAGTGAATGGCGGTAAG | 59 |
| | | | | Lower Seq: GTATATCCCGACAATAGTCCTG | 60 |
| | | | | SNP primer: GTACATGATAATACAGCAAAGATT | 61 |

An F1 hybrid obtained by using the rice male sterile line containing the Habataki-derived hd1 gene as a seed parent contains the Habataki-derived hd1 gene and therefore becomes an early season cultivar, as compared to an F1 hybrid obtained by using a Koshihikari male sterile line as a seed parent. For this reason, in the method for producing a rice F1 seed in accordance with the present invention, by using a rice male sterile line containing the Habataki-derived hd1 gene, seeds of an F1 hybrid for which the heading time could be made earlier can be efficiently produced, and efficiency of a combinatorial test for rearing an F1 hybrid can be improved.

The near-isogenic line of *Oryza sativa* L. cultivar Koshihikari in which two or more genes of the sd1 gene, the Gn1 cultivar Koshihikari in which the sd1 gene, the Gn1 gene, and the hd1 gene have been substituted with genes derived from Habataki (Habataki-derived sd1/Habataki-derived Gn1/Habataki-derived hd1-containing near-isogenic line) may be created by crossing a Habataki-derived sd1/Habataki-derived Gn1-containing near-isogenic line and a Habataki-derived hd1-containing near-isogenic line, and selecting an individual in which all of the region in which the sd1 gene is encoded, the region in which the Gn1 gene is encoded, and the region in which hd1 gene is encoded are a region derived from Habataki, in homologous chromosomes of both parties, using a DNA marker as an indicator, from the second filial generation (F2 hybrid) obtained by self-mating the resulting F1 hybrid.

The rice male sterile line used in the present invention may be a line exhibiting semi-waxiness. The rice male sterile line exhibiting semi-waxiness may be obtained by backcrossing a near-isogenic line of *Oryza sativa* L. cultivar Koshihikari exhibiting semi-waxiness twice with a male sterile line, and selecting a rice individual exhibiting semi-waxiness in every seed from the resulting F3 hybrid.

Through the introduction of a chromosome fragment having a semi-waxiness gene, by lowering an amylose content of brown rice, a taste quality may be improved. In particular, in an F1 hybrid line which is rendered such that only one parent has a semi-waxiness mutant gene, since brown rice exhibiting semi-waxiness and brown rice having a common characteristic appear in a ratio of 1:3, a mild low-amylose content can be achieved, and a taste quality becomes superior to Koshihikari with no semi-waxiness. Therefore, in the method for producing a rice F1 seed in accordance with the present invention, by using a near-isogenic line of *Oryza sativa* L. cultivar Koshihikari exhibiting semi-waxiness, seeds of an F1 hybrid with an improved taste quality can be efficiently produced, and efficiency of a combinatorial test for rearing an F1 hybrid can be improved.

The near-isogenic line of *Oryza sativa* L. cultivar Koshihikari exhibiting semi-waxiness may be obtained, for example, from a mutant group of *Oryza sativa* L. cultivar Koshihikari by the selection depending on a phenotypic characteristic expressing semi-waxiness, or a gene contributing to semi-waxiness (semi-waxiness gene) using a DNA marker. The semi-waxiness gene may be, for example, a waxy-mq gene present in the chromosome 6 of *Oryza saliva* L. cultivar. Further, the near-isogenic line of *Oryza saliva* L. cultivar Koshihikari exhibiting semi-waxiness may be a mutant of known *Oryza sativa* L. cultivar Koshihikari such as *Oryza sativa* L. cultivar Milky Queen which is mutant of a waxy-mq gene, or a near-isogenic line obtained by continuous backcrossing of *Oryza sativa* L. cultivar Koshihikari with semi-waxiness-expressing *Oryza sativa* L. cultivar other than *Oryza sativa* L. cultivar Koshihikari (for example, mutants derived from other cultivar).

The rice male sterile line used in the present invention may be a line which contains one or more genes selected from the group consisting of the sd1 gene derived from *Oryza sativa* L. cultivar Habataki, the Gn1 gene derived from *Oryza sativa* L. cultivar Habataki and the hd1 gene derived from *Oryza sativa* L. cultivar Habataki, and also exhibits semi-waxiness. The rice male sterile line exhibiting semi-waxiness may be created, specifically, in the following manner. First, a near-isogenic line of *Oryza sativa* L. cultivar Koshihikari in which at least one or more genes of the sd1 gene, the Gn1 gene and the hd1 gene have been substituted with Habataki-derived genes and a near-isogenic line of *Oryza sativa* L. cultivar Koshihikari exhibiting semi-waxiness are mated, and a rice individual in which at least one or more genes of the sd1 gene, the Gn1 gene and the hd1 gene have been substituted with Habataki-derived genes and which also exhibits semi-waxiness is selected from the F2 hybrid obtained by self-mating the resulting F1 hybrid. Then, the thus-obtained rice individual and a Koshihikari male sterile line are mated, and the resulting F1 hybrid is subjected to continuous backcrossing, thereby obtaining a rice male sterile line in which at least one or more genes of the sd1 gene, the Gn1 gene and the hd1 gene have been substituted with Habataki-derived genes and which also exhibits semi-waxiness.

The rice fertility restorer line used as a pollen parent in the method for producing a rice F1 seed in accordance with the present invention is not particularly limited as long as it is a rice plant line which is capable of restoring fertility of a rice male sterile line used as a seed parent. Where the seed parent is of BT-type cytoplasmic male sterility, examples of the rice fertility restorer line include *Oryza saliva* L. cultivar JFR-4, *Oryza sativa* L. cultivar ST-1, *Oryza sativa* L. cultivar ST-2, *Oryza sativa* L. cultivar ST-4, *Oryza sativa* L. cultivar Takanari, *Oryza sativa* L. cultivar Guichao 2, *Oryza sativa* L. cultivar Shui-Yuan 258, and *Oryza sativa* L. cultivar Habataki. Further, whether or not a certain *Oryza saliva* L. cultivar is a rice fertility restorer line for a certain Koshihikari male sterile line may be investigated by crossing this *Oryza saliva* L. cultivar and the Koshihikari male sterile line, and examining male fertility of the resulting F1 hybrid. In the case where male sterility has been restored in the F1 hybrid, the *Oryza sativa* L. cultivar is found to be a rice fertility restorer line for the Koshihikari male sterile line. Further, in the case where the seed parent is of an environmental condition-dependent male sterile line, any rice line may be used as a rice fertility restorer line as long as it is a rice plant line not containing a mutant gene responsible for male sterility that the seed parent has possessed. This is because the mutant gene does not express a mutant characteristic in F1 (hetero state).

In the method for producing a rice F1 seed in accordance with the present invention, the crossing of a rice male sterile line containing one or more genes selected from the group consisting of the sd1 gene derived from *Oryza sativa* L. cultivar Habataki, the Gn1 gene derived from *Oryza sativa* L. cultivar Habataki, and the hd1 gene derived from *Oryza sativa* L. cultivar Habataki with a rice fertility restorer line as a pollen parent may be carried out by natural mating or artificial mating.

EXAMPLES

The present invention will now be described in more detail with reference to Examples, but the present invention is not limited to the following Examples.

Example 1

<Near-isogenic Line of *Oryza saliva* L. Cultivar Koshihikari>

As a near-isogenic line of *Oryza saliva* L. cultivar Koshihikari for creating a rice male sterile line which is used as a seed parent, an *Oryza saliva* L. cultivar Koshihikari eichi 2go, an *Oryza saliva* L. cultivar Koshihikari eichi 2go_long region, an *Oryza sativa* L. cultivar Koshihikari eichi 3go, an *Oryza sativa* L. cultivar Koshihikari eichi 4go, an *Oryza sativa* L. cultivar Koshihikari eichi 4go_long region, an *Oryza sativa* L. cultivar Koshihikari kazusa 1go, an *Oryza sativa* L. cultivar Koshihikari kazusa 2go, an *Oryza sativa* L. cultivar Koshihikari kazusa 3go, and an *Oryza saliva* L. cultivar Koshihikari kazusa 4go were obtained.

Among these near-isogenic lines, an *Oryza sativa* L. cultivar Koshihikari eichi 2go, an *Oryza sativa* L. cultivar Koshihikari eichi 3go, an *Oryza saliva* L. cultivar Koshihikari eichi 4go, and an *Oryza sativa* L. cultivar Koshihikari kazusa 4go (deposit number: FERM P-21596) used herein were those disclosed in Patent Document 3 and Patent Document 4. These lines were reared after several times of backcrossing of Koshihikari into Habataki, followed by DNA marker selection. The positional relationship between the Habataki-derived chromosome fragment-substituted region in a chromosome of *Oryza sativa* L. cultivar Koshihikari eichi 4go and the DNA markers given in Table 1 is as shown in the second step of FIG. 1; the positional relationship between the Habataki-derived chromosome fragment-substituted region in a chromosome of *Oryza sativa* L. cultivar Koshihikari eichi 2go and the DNA markers given in Table 2 is as shown in the second step of FIG. 2; and the positional relationship between the Habataki-derived chromosome fragment-substituted region in a chromosome of *Oryza sativa* L. cultivar Koshihikari eichi 3go and the DNA markers given in Table 3 is as shown in the middle step of FIG. 3.

Further, according to the method described in Patent Document 3, an *Oryza sativa* L. cultivar Koshihikari eichi 4go_long region in which the region longer than *Oryza sativa* L. cultivar Koshihikari eichi 4go has been substituted with a Habataki-derived chromosome fragment was created. More specifically, an individual having a desired genome was selected using SP-4009, G2003, G2002, SP-1259, and SP-477 among DNA markers described in Table 1.

Specifically, *Oryza sativa* L. cultivar Koshihikari was backcrossed several times with *Oryza sativa* L. cultivar Habataki. A seed of the resulting hybrid was further cultivated, and a seedling was grown to such an extent that the seedling could be transplanted to an agricultural field. DNA was extracted from a leaf of each cultivated individual, and one cultivated individual in which SP-4009 and SP-477 are a homo-chromosome region of an allele derived from Koshihikari, and G2003, G2002, and SP-1259 are a homo-chromosome region of an allele derived from Habataki was selected. This selected cultivated individual is a new cultivar in which the region containing the sd1 gene was substituted with a Habataki-derived chromosome fragment. The present inventors designated this new cultivar as "*Oryza sativa* L. cultivar Koshihikari eichi 4go_long region". The positional relationship between the Habataki-derived chromosome fragment-substituted region in a chromosome of *Oryza sativa* L. cultivar Koshihikari eichi 4go_long region and the DNA markers given in Table 1 is as shown in the third step of FIG. 1.

In the same manner, according to the method described in Patent Document 3, an *Oryza sativa* L. cultivar Koshihikari eichi 2go_long region in which the region longer than *Oryza sativa* L. cultivar Koshihikari eichi 2go has been substituted with a Habataki-derived chromosome fragment was created. More specifically, an individual having a desired genome was selected using SP-156, SP-2032, SP-4028, SP-4038, and SP-4030 among DNA markers described in Table 2.

Specifically, *Oryza sativa* L. cultivar Koshihikari was backcrossed several times with *Oryza sativa* L. cultivar Habataki. A seed of the resulting hybrid was further cultivated, and a seedling was grown to such an extent that the seedling could be transplanted to an agricultural field. DNA was extracted from a leaf of each cultivated individual, and one cultivated individual in which SP-156 and SP-4030 are a homo-chromosome region of an allele derived from Koshihikari, and SP-2032, SP-4028, and SP-4038 are a homo-chromosome region of an allele derived from Habataki was selected. This selected cultivated individual is a new cultivar in which the region containing the Gn1 gene was substituted with a Habataki-derived chromosome fragment. The present inventors designated this new cultivar as "*Oryza sativa* L. cultivar Koshihikari eichi 2go_long region". The positional relationship between the Habataki-derived chromosome fragment-substituted region in a chromosome of *Oryza sativa* L. cultivar Koshihikari eichi 2go_long region and the DNA markers given in Table 2 is as shown in the third step of FIG. 2.

Further, a near-isogenic line in which the sd1 gene and the hd1 gene are genes derived from Habataki was created. Specifically, *Oryza sativa* L. cultivar Koshihikari eichi 4go and *Oryza sativa* L. cultivar Koshihikari eichi 3go were mated, and 2 individuals out of the resulting progeny individuals (seeds) were cultivated and self-fertilized (self-mated) to further harvest 100 seeds which are progeny individuals. All of these 100 seeds were cultivated, and a DNA marker of each progeny individual was investigated. One cultivated individual in which SP-462[M4(sd1)] is a homo-chromosome region of an allele derived from Habataki, and SP-2254[M3(hd1)] is a homo-chromosome region of an allele derived from Habataki was selected. This selected cultivated individual is a new cultivar in which all of the region containing the sd1 gene and the region containing the hd1 gene were substituted with a Habataki-derived chromosome fragment (homo). The present inventors designated this new cultivar as "*Oryza saliva* L. cultivar Koshihikari kazusa 1go".

Further, a near-isogenic line in which the Gn1 gene and the hd1 gene are genes derived from Habataki was created. Specifically, *Oryza sativa* L. cultivar Koshihikari eichi 2go and *Oryza sativa* L. cultivar Koshihikari eichi 3go were mated, and 2 individuals out of the resulting progeny individuals (seeds) were cultivated and self-fertilized (self-mated) to further harvest 100 seeds which are progeny individuals. All of these 100 seeds were cultivated, and a DNA marker of each progeny individual was investigated. One cultivated individual in which SP-4028[M4(Gn1)] is a homo-chromosome region of an allele derived from Habataki, and SP-2254 [M3(hd1)] is a homo-chromosome region of an allele derived from Habataki was selected. This selected cultivated individual is a new cultivar in which all of the region containing the Gn1 gene and the region containing the hd1 gene were substituted with a Habataki-derived chromosome fragment (homo). The present inventors designated this new cultivar as "*Oryza sativa* L. cultivar Koshihikari kazusa 2go".

Further, a near-isogenic line in which the sd1 gene and the Gn1 gene are genes derived from Habataki was created. Specifically, *Oryza sativa* L. cultivar Koshihikari eichi 4go and *Oryza sativa* L. cultivar Koshihikari eichi 2go were mated, and 2 individuals out of the resulting progeny individuals (seeds) were cultivated and self-fertilized (self-mated) to further harvest 100 seeds which are progeny individuals. All of these 100 seeds were cultivated, and a DNA marker of each progeny individual was investigated. One cultivated individual in which SP-462[M4(sd1)] is a homo-chromosome region of an allele derived from Habataki, and SP-4028[M4(Gn1)] is a homo-chromosome region of an allele derived from Habataki was selected. This selected cultivated individual is a new cultivar in which all of the region containing the sd1 gene and the region containing the Gn1 gene were substituted with a Habataki-derived chromosome fragment (homo). The present inventors designated this new cultivar as "*Oryza sativa* L. cultivar Koshihikari kazusa 3go".

Figure 4:
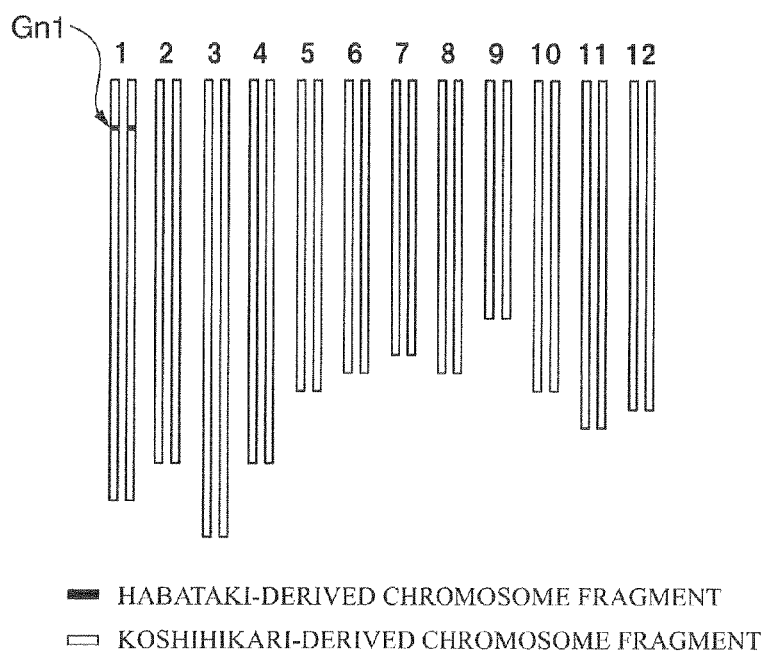
FIG. 4 is a view schematically showing a genome of *Oryza sativa* L. cultivar Koshihikari eichi 2go used in Example 1.
Figure 5:
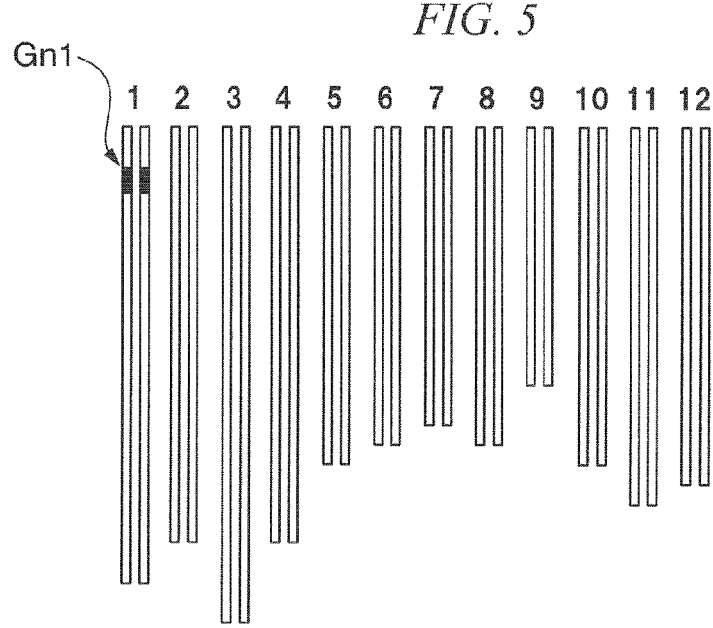
FIG. 5 is a view schematically showing a genome of *Oryza saliva* L. cultivar Koshihikari eichi 2go_long region used in Example 1.
Figure 6:
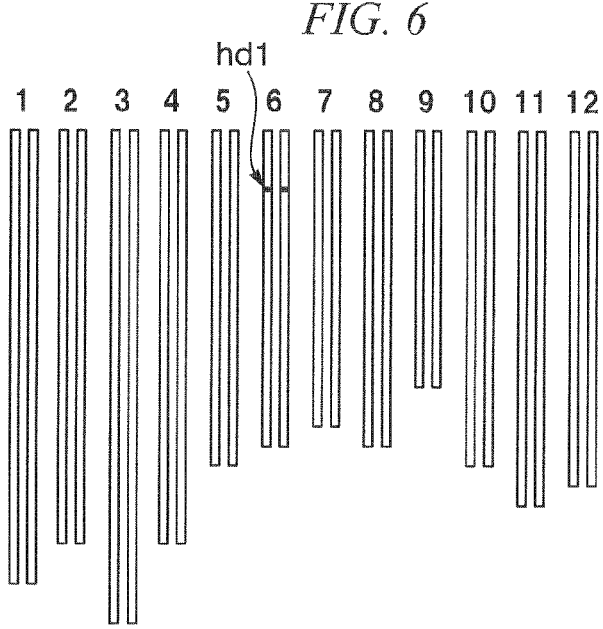
FIG. 6 is a view schematically showing a genome of *Oryza saliva* L. cultivar Koshihikari eichi 3go used in Example 1.
Figure 7:
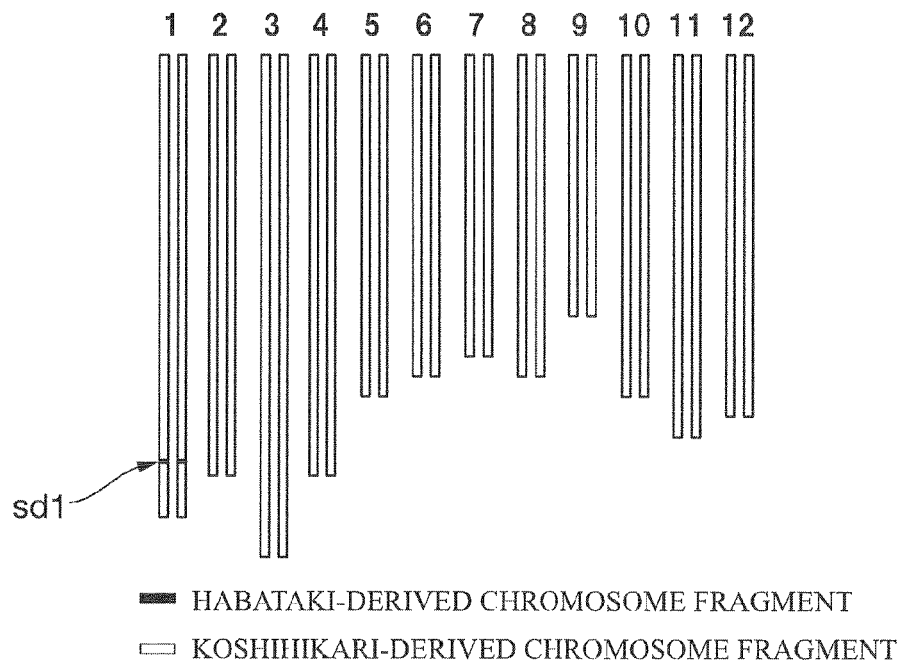
FIG. 7 is a view schematically showing a genome of *Oryza sativa* L. cultivar Koshihikari eichi 4go used in Example 1.
Figure 8:
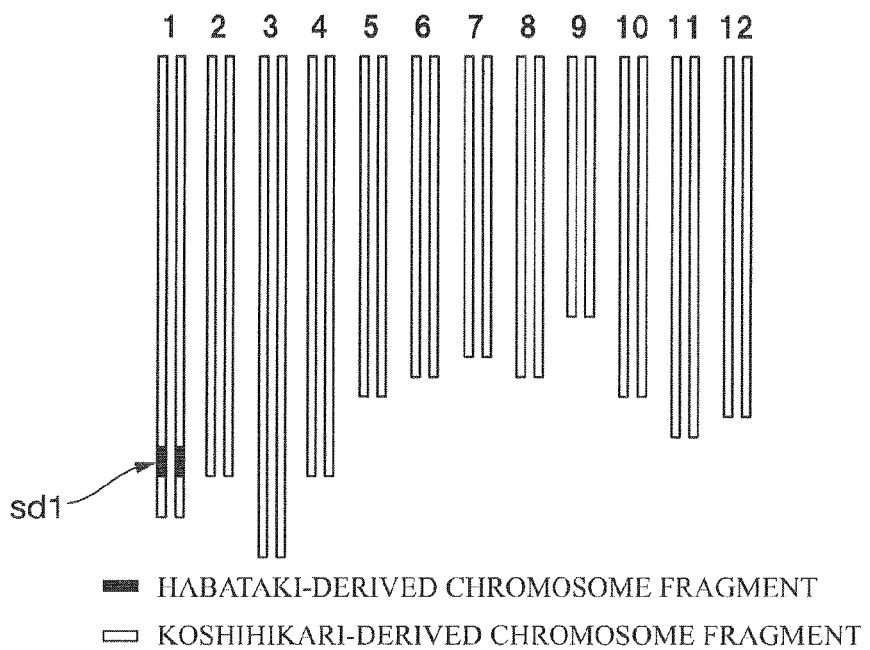
FIG. 8 is a view schematically showing a genome of *Oryza saliva* L. cultivar Koshihikari eichi 4go_long region used in Example 1.
Figure 9:
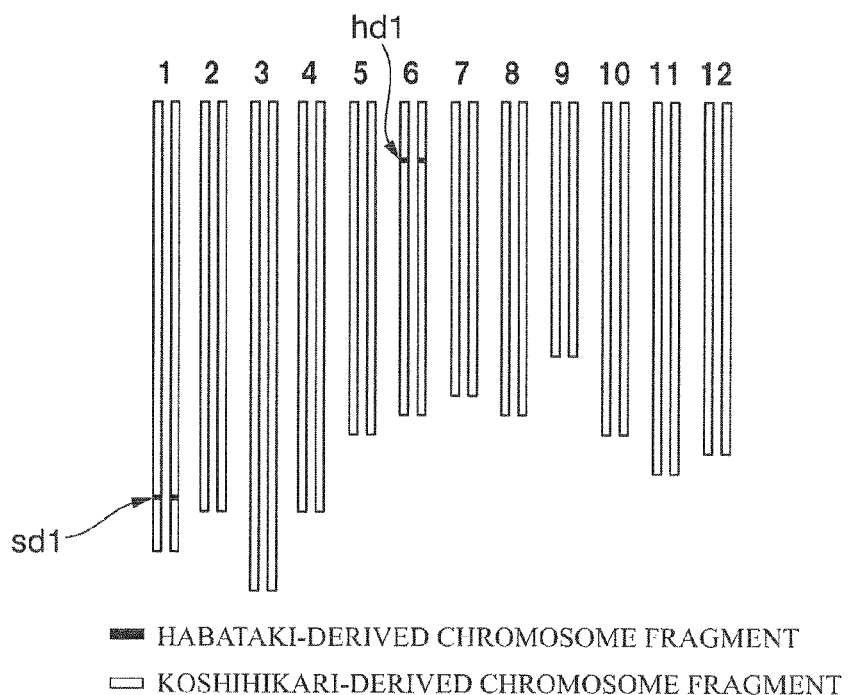
FIG. 9 is a view schematically showing a genome of *Oryza saliva* L. cultivar Koshihikari kazusa 1go used in Example 1.
Figure 10:
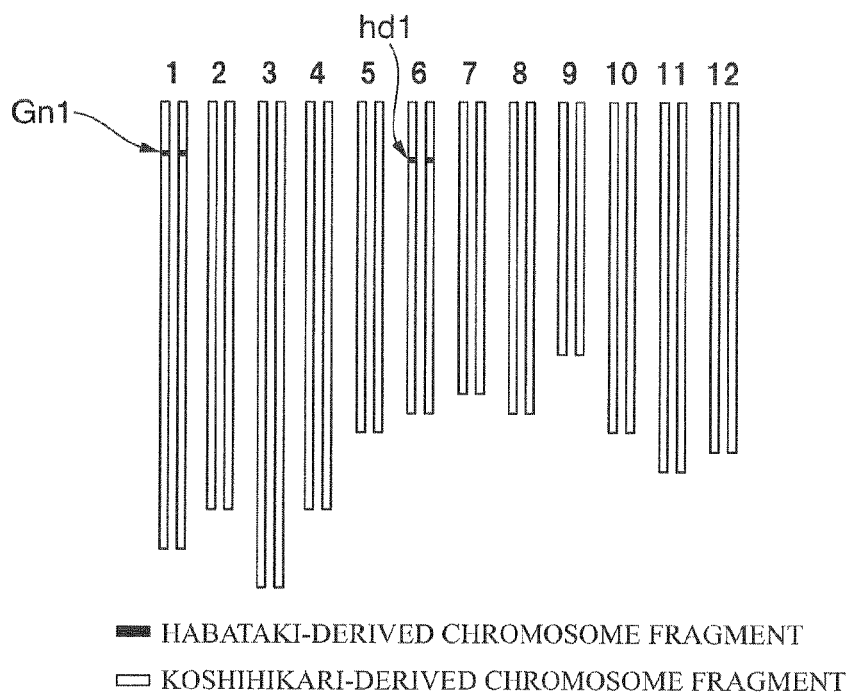
FIG. 10 is a view schematically showing a genome of *Oryza sativa* L. cultivar Koshihikari kazusa 2go used in Example 1.
Figure 11:
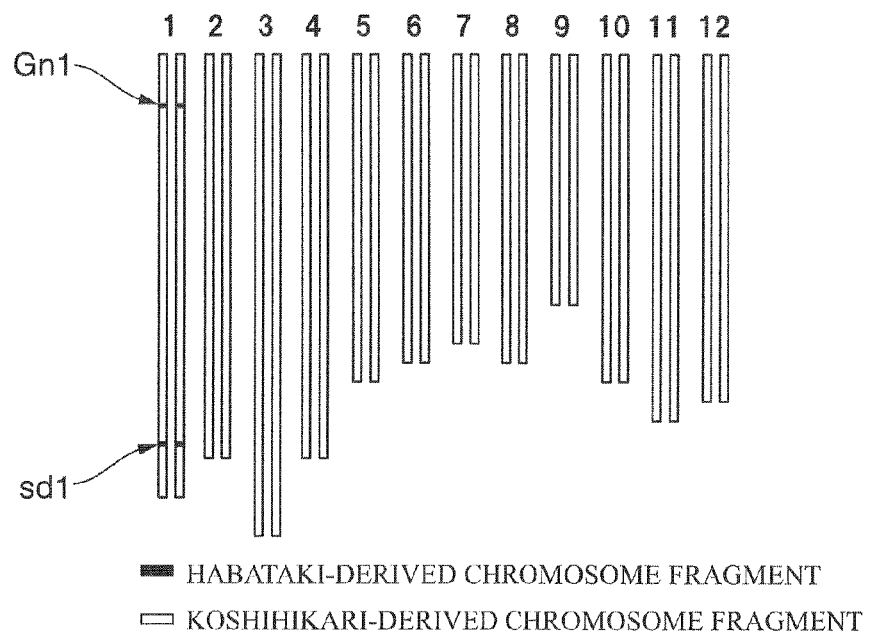
FIG. 11 is a view schematically showing a genome of *Oryza sativa* L. cultivar Koshihikari kazusa 3go used in Example 1.

FIG. 4 schematically shows a genome of *Oryza sativa* L. cultivar Koshihikari eichi 2go; FIG. 5 schematically shows a genome of *Oryza sativa* L. cultivar Koshihikari eichi 2go_long region; FIG. 6 schematically shows a genome of *Oryza sativa* L. cultivar Koshihikari eichi 3go; FIG. 7 schematically shows a genome of *Oryza sativa* L. cultivar Koshihikari eichi 4go; FIG. 8 schematically shows a genome of *Oryza sativa* L. cultivar Koshihikari eichi 4go_long region; FIG. 9 schematically shows a genome of *Oryza sativa* L. cultivar Koshihikari kazusa 1go; FIG. 10 schematically shows a genome of *Oryza sativa* L. cultivar Koshihikari kazusa 2go; and FIG. 11 schematically shows a genome of *Oryza sativa* L. cultivar Koshihikari kazusa 3go.

<Cytoplasmic Male Sterile Line of *Oryza sativa* L. Cultivar Koshihikari (CMS-Koshihikari)>

*Oryza sativa* L. cultivar Koshihikari was backcrossed 6 times with *Oryza sativa* L. cultivar CHINSURAH BORO 2, CMS-Koshihikari exhibiting the same characteristic equivalent to Koshihikari except that a growth property in an agricultural field is male sterility was reared.

<Cytoplasmic Male Sterile Line of *Oryza sativa* L. Cultivar Milky Queen (CMS-Milky Queen)>

Using CMS-Koshihikari as a seed parent, Milky Queen which is a semi-waxiness mutant of Koshihikari was backcrossed twice to obtain seeds in which a brown rice characteristic is segregated into a non-waxy type and a semi-waxy type. Then, brown rice exhibiting semi-waxiness was selected from these seeds. This selected brown rice is a cytoplasmic male sterile line of *Oryza sativa* L. cultivar Koshihikari having semi-waxiness. That line was reared as CMS-Milky Queen.

<Rice Cytoplasmic Male Sterile Line (CMS Line)>

Continuous backcrossing was carried out using CMS-Koshihikari as a seed parent and using an *Oryza sativa* L. cultivar Koshihikari eichi 2go, an *Oryza sativa* L. cultivar Koshihikari eichi 2go_long region, an *Oryza sativa* L. cultivar Koshihikari eichi 3go, an *Oryza sativa* L. cultivar Koshihikari eichi 4go, an *Oryza saliva* L. cultivar Koshihikari eichi 4go_long region, an *Oryza saliva* L. cultivar Koshihikari kazusa 2go, an *Oryza saliva* L. cultivar Koshihikari kazusa 3go, or an *Oryza sativa* L. cultivar Koshihikari kazusa 4go as a pollen parent. Among the resulting progeny individuals, a cultivated individual exhibiting male sterility was selected. DNA was extracted from a leaf of each selected cultivated individual, and a DNA marker was investigated. Each one of cultivated individuals in which the same region as a pollen parent is a homo-chromosome region of an allele derived from a foreign cultivar was selected. These selected cultivated individuals are a new cultivar having fundamentally the same characteristic as the pollen parent, except that they are of male sterility. The present inventors designated the rice cytoplasmic male sterile line obtained by using Oryza *sativa* L. cultivar Koshihikari eichi 2go as a pollen parent as "CMS-*Oryza sativa* L. cultivar Koshihikari eichi 2go"; the rice cytoplasmic male sterile line obtained by using *Oryza sativa* L. cultivar Koshihikari eichi 2go_long region as a pollen parent as "CMS-*Oryza saliva* L. cultivar Koshihikari eichi 2go_long region"; the rice cytoplasmic male sterile line obtained by using *Oryza sativa* L. cultivar Koshihikari eichi 3go as a pollen parent as "CMS-*Oryza sativa* L. cultivar Koshihikari eichi 3go"; the rice cytoplasmic male sterile line obtained by using *Oryza sativa* L. cultivar Koshihikari eichi 4go as a pollen parent as "CMS-*Oryza sativa* L. cultivar Koshihikari eichi 4go"; the rice cytoplasmic male sterile line obtained by using *Oryza sativa* L. cultivar Koshihikari eichi 4go_long region as a pollen parent as "CMS-*Oryza sativa* L. cultivar Koshihikari eichi 4go_long region"; the rice cytoplasmic male sterile line obtained by using *Oryza sativa* L. cultivar Koshihikari kazusa 1go as a pollen parent as "CMS-*Oryza sativa* L. cultivar Koshihikari kazusa 1go"; the rice cytoplasmic male sterile line obtained by using *Oryza sativa* L. cultivar Koshihikari kazusa 2go as a pollen parent as "CMS-*Oryza saliva* L. cultivar Koshihikari kazusa 2go"; and the rice cytoplasmic male sterile line obtained by using *Oryza sativa* L. cultivar Koshihikari kazusa 3go as a pollen parent as "CMS-*Oryza sativa* L. cultivar Koshihikari kazusa 3go", respectively.

Further, among new cultivars obtained in Example 1, the present applicant has deposited CMS-*Oryza sativa* L. cultivar Koshihikari eichi 2go, CMS-*Oryza sativa* L. cultivar Koshihikari eichi 3go, CMS-*Oryza sativa* L. cultivar Koshihikari eichi 4go, CMS-*Oryza sativa* L. cultivar Koshihikari kazusa 1go, CMS-*Oryza sativa* L. cultivar Koshihikari kazusa 2go, and CMS-*Oryza sativa* L. cultivar Koshihikari kazusa 3go as a novel plant in the International Patent Organism Depositary, National Institute of Advanced Industrial Science and Technology (Tsukuba Center Chuou 6th, Higashi 1-1-1, Tsukuba-shi, Ibaraki-ken, Japan). The representative seeds of the rice cytoplasmic male sterile lines CMS-Koshihikari eichi 2go, CMS-Koshihikari eichi 3go, CMS-Koshihikari eichi 4go, CMS-Koshihikari kazusa 1go, CMS-Koshihikari kazusa 2go, and CMS-Koshihikari kazusa 3go are deposited under accession numbers FERM ABP-22217, FERM ABP-22280, FERM ABP-22322, FERM ABP-22323, FERM ABP-22303, and FERM ABP-22218, respectively. The seeds will be irrevocably and without restriction or condition, released to the public upon the issuance of a patent from the instant application.

<Production of F1 Seed>

Each of the above-obtained rice cytoplasmic male sterile lines (CMS lines) as a seed parent, and an independently reared restorer intermediate seed parent line ST-1, ST-2 or ST-4 as a pollen parent were mated to harvest a seed of F1 hybrid. As a control, a seed of F1 hybrid was harvested by mating CMS-Koshihikari as a seed parent and ST-1, ST-2 or ST-4 as a pollen parent were mated to obtain seeds of an F1 hybrid. The F1 seeds thus obtained were cultivated and subjected to study of characteristic in a field test implemented in Aichi Prefecture in 2006, 2007 and 2008. Study of characteristics was carried out according to Property Examination for filing Variety Registration based on The Plant Variety Protection and Seed Act (Act No. 83 of 1998), Article 5(1).

<Culm Length of F1 Hybrid>

Figure 12:
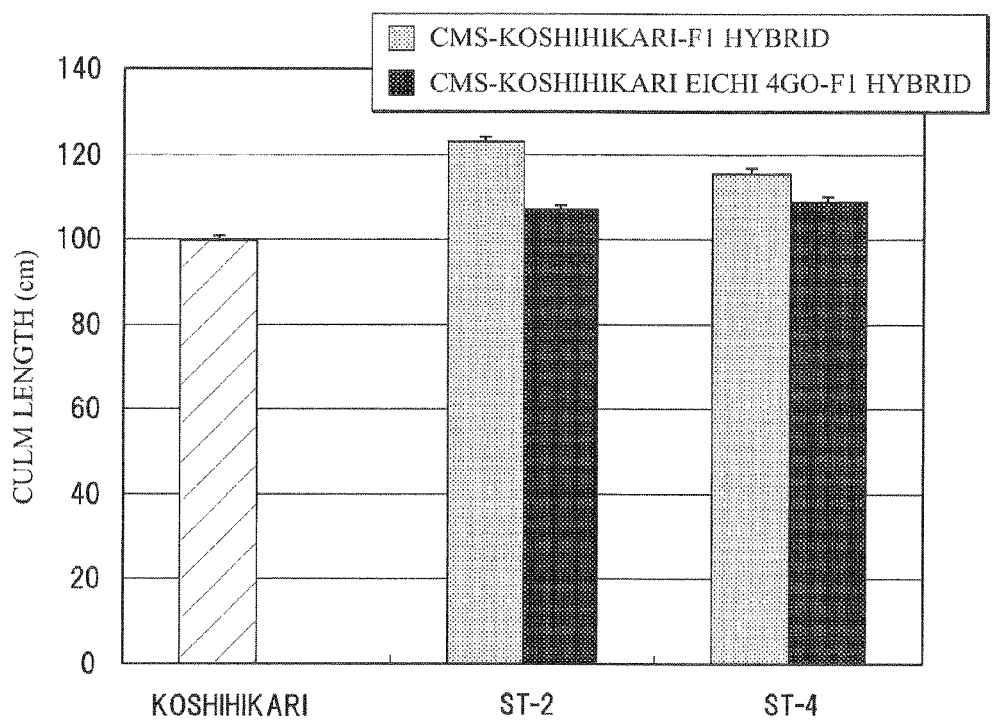
FIG. 12 is a view showing the measurement results of a culm length performed in Example 1 for an F1 hybrid obtained using CMS-Koshihikari eichi 4go as a seed parent, an F1 hybrid obtained using CMS-Koshihikari as a seed parent, and *Oryza sativa* L. cultivar Koshihikari.

A culm length was compared between the F1 hybrid obtained using CMS-Koshihikari eichi 4go as a seed parent, the F1 hybrid obtained using CMS-Koshihikari as a seed parent, and *Oryza saliva* L. cultivar Koshihikari. The measurement results of the culm length of each line are shown in FIG. 12. As a result, the culm length of Koshihikari which is a control cultivar was 99.6 cm, whereas the culm length of the F1 hybrid obtained by mating CMS-Koshihikari and ST-2 or ST-4 was 123.0 cm or 115.3 cm, respectively. On the other hand, the culm length of the F1 hybrid obtained by mating CMS-Koshihikari eichi 4go and ST-2 or ST-4 was 106.9 cm or 108.8 cm, respectively, which is 6.5 to 16.1 cm shorter than the F1 hybrid obtained by using CMS-Koshihikari as a seed parent, in conjunction with a reduction of lodging upon harvesting. Further, the F1 hybrid line obtained by using Koshihikari eichi 4go as a seed parent exhibited the same characteristic as the F1 hybrid line obtained by using Koshihikari as a seed parent, except that the culm length became shorter.

Figure 13:
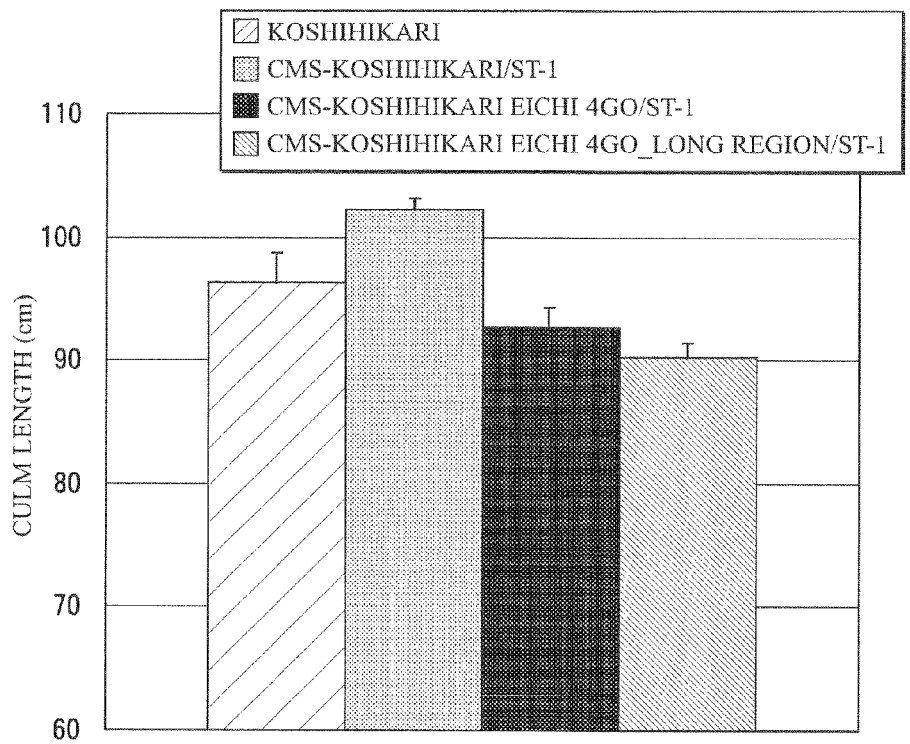
FIG. 13 is a view showing the measurement results of a culm length performed in Example 1 for an F1 hybrid obtained from CMS-Koshihikari and ST-1, an F1 hybrid obtained from CMS-Koshihikari eichi 4go and ST-1, an F1 hybrid obtained from CMS-Koshihikari eichi 4go_long region and ST-1, and *Oryza sativa* L. cultivar Koshihikari.

In different year, the culm length was measured and compared between the F1 hybrid obtained from CMS-Koshihikari and ST-1, the F1 hybrid obtained from CMS-Koshihikari eichi 4go and ST-1, the F1 hybrid obtained from CMS-Koshihikari eichi 4go_long region and ST-1, and *Oryza sativa* L. cultivar Koshihikari. The measurement results of the culm length of each line are shown in FIG. 13. As a result, the culm length of the F1 hybrid obtained by using CMS-Koshihikari as a seed parent was longer than the culm length of Koshihikari which is a control cultivar, whereas the culm length of the F1 hybrid obtained by using CMS-Koshihikari eichi 4go or CMS-Koshihikari eichi 4go_long region as a seed parent was shorter than the culm length of Koshihikari. Further, when the F1 hybrid obtained from CMS-Koshihikari eichi 4go and the F1 hybrid obtained from CMS-Koshihikari eichi 4go_long region were compared, there was no significant difference therebetween.

From these results, it is clear that, by using the rice male sterile line the region in which the sd1 gene is encoded has been substituted with a Habataki-derived chromosome fragment, an F1 hybrid with a shorter culm length and an improved lodging resistance can be obtained, as compared to when the rice male sterile line having no Habataki-derived sd1 gene was used.

<Days to Heading of F1 Hybrid>

Figure 14:
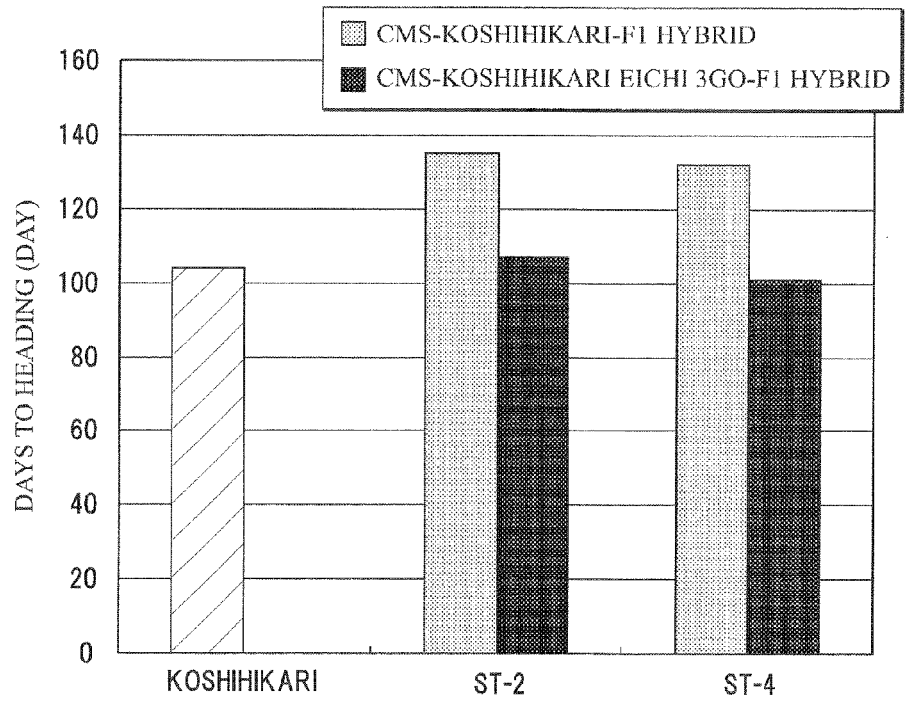
FIG. 14 is a view showing the measurement results of days to heading of an F1 hybrid obtained using CMS-Koshihikari eichi 3go or CMS-Koshihikari as a seed parent and using ST-2 or ST-4 as a pollen parent in Example 1.

An F1 hybrid was obtained using CMS-Koshihikari eichi 3go or CMS-Koshihikari as a seed parent and using ST-2 or ST-4 as a pollen parent, and days to heading of the resulting F1 hybrid were investigated. The measurement results of days to heading of each line are shown in FIG. 14. In this test in which seeds were sowed on April 16, days to heading of the control cultivar Koshihikari were 104 days, whereas days to heading of the F1 hybrids obtained from CMS-Koshihikari and ST-2 or ST-4 were 135 days or 132 days. On the other hand, the F1 hybrids obtained from CMS-Koshihikari eichi 3go and ST-2 or ST-4 exhibited days to heading of 107 days or 101 days which are approximately 10 to 28 days fewer than those of the F1 hybrid obtained by using CMS-Koshihikari as a seed parent, and became converted to have earlier growth. As described above, the F1 hybrid obtained by using CMS-Koshihikari eichi 3go as a seed parent exhibited virtually the same number of days to heading as Koshihikari, and showed a period of maturity adaptable to cultivation in Aichi Prefecture. Further, the characteristic of the F1 hybrid line obtained by using CMS-Koshihikari eichi 3go as a seed parent exhibited a tendency toward plants being small due to decreasing days to heading and being converted to have earlier growth, but other characteristics were fundamentally the same as the F1 hybrid obtained by using CMS-Koshihikari as a seed parent.

From these results, it is clear that, by using the rice cytoplasmic male sterile line where the region in which the hd1 gene is encoded has been substituted with a Habataki-derived chromosome fragment, an F1 hybrid converted to have earlier growth can be obtained, as compared to when the rice cytoplasmic male sterile line having no Habataki-derived hd1 gene was used.

<Grain Number of F1 Hybrid>

Figure 15:
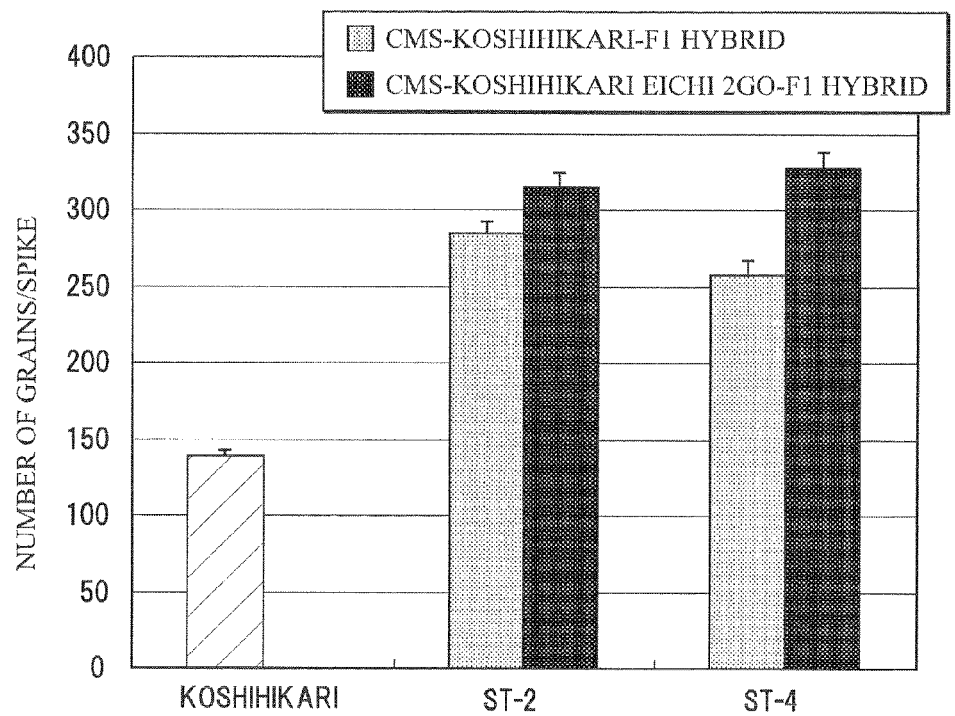
FIG. 15 is a view showing the measurement results of the number of grains/spike of an F1 hybrid obtained using CMS-Koshihikari eichi 2go or CMS-Koshihikari as a seed parent and using ST-2 or ST-4 as a pollen parent in Example 1.

An F1 hybrid was obtained using CMS-Koshihikari eichi 2go or CMS-Koshihikari as a seed parent and using ST-2 or ST-4 as a pollen parent, and the grain number of these F1 hybrids was investigated. The measurement results of the grain number of each line are shown in FIG. 15. As a result, the number of grains/spike in main stem of Koshihikari which is a control cultivar was 138.5 grains, whereas the number of grains/spike in main stem of the F1 hybrid obtained from CMS-Koshihikari and ST-2 or ST-4 was 284.0 grains or 257.4 grains, respectively. On the other hand, the F1 hybrid obtained from CMS-Koshihikari eichi 2go and ST-2 or ST-4 exhibited the number of grains/spike of 314.8 grains or 327.0 grains, respectively, which are 30 to 70 grains greater than the F1 hybrid obtained by using CMS-Koshihikari as a seed parent, and showed improvement of weight/spike and yield performance. Further, the characteristic of the F1 hybrid line obtained by using CMS-Koshihikari eichi 2go as a seed parent was fundamentally the same as the F1 hybrid obtained by using CMS-Koshihikari as a seed parent, except that the grain number was increased.

Figure 16:
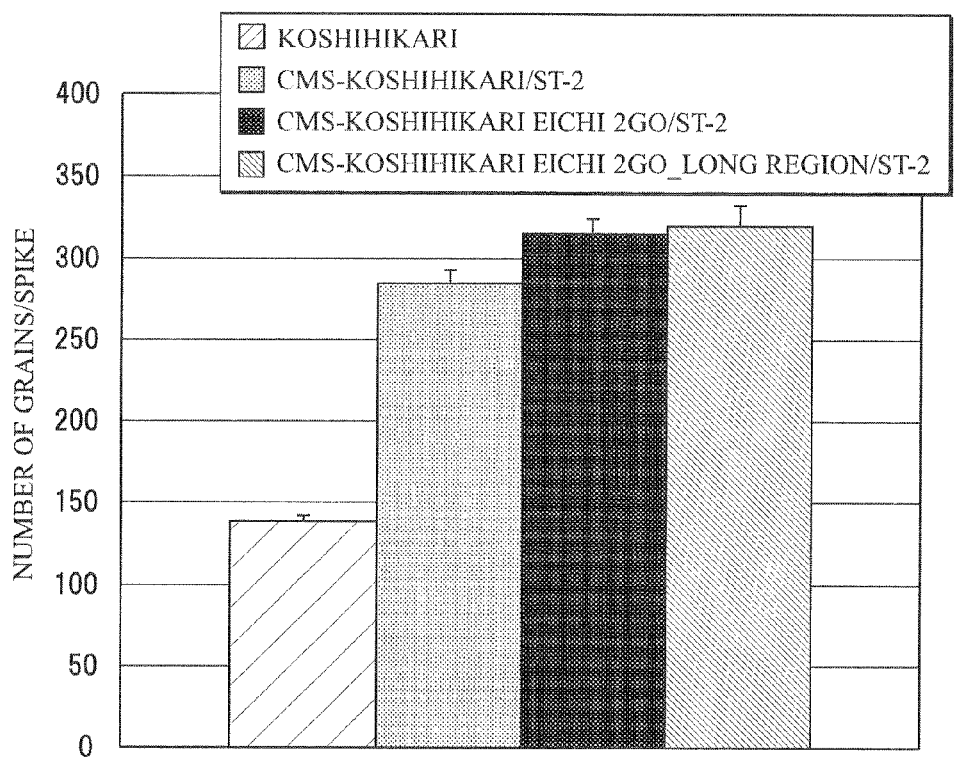
FIG. 16 is a view showing the measurement results of the number of grains/spike of an F1 hybrid obtained using CMS-Koshihikari eichi 2go, CMS-Koshihikari eichi 2go_long region, or CMS-Koshihikari as a seed parent and using ST-2 as a pollen parent in Example 1.

Further, grain numbers of the F1 hybrid obtained by using CMS-Koshihikari eichi 2go, CMS-Koshihikari eichi 2go_long region, or CMS-Koshihikari as a seed parent and using ST-2 as a pollen parent were measured and compared. The measurement results of the grain number of each line are shown in FIG. 16. As a result, when the number of grains/spike was compared between the F1 hybrid obtained from CMS-Koshihikari eichi 2go and the F1 hybrid obtained from CMS-Koshihikari eichi 2go_long region, there was no significant difference therebetween.

<Characteristics of F1 Hybrid Line Obtained from Rice Cytoplasmic Male Sterile Line with Substitution of Plural Genes>

The culm length, the number of grains/spike, and days to heading of the F1 hybrid, which was obtained using CMS-Koshihikari, CMS-Koshihikari eichi 2go, CMS-Koshihikari eichi 3go, CMS-Koshihikari eichi 4go, CMS-Koshihikari kazusa 1go, CMS-Koshihikari kazusa 2go, or CMS-Koshihikari kazusa 3go as a seed parent and using ST-2 as a pollen parent, are shown in Table 4. The results of Koshihikari as a control are also shown therein. As a result, the F1 hybrid line obtained from CMS-Koshihikari kazusa 1go and CMS-Koshihikari kazusa 3go containing the Habataki-derived sd1 gene exhibited a significantly shorter culm length than the F1 hybrid line obtained from CMS-Koshihikari, similar to the F1 hybrid line obtained from CMS-Koshihikari eichi 4go. Further, the F1 hybrid lines obtained from CMS-Koshihikari kazusa 1go and CMS-Koshihikari kazusa 2go containing the Habataki-derived hd1 gene exhibited fewer days to heading than the F1 hybrid line obtained from CMS-Koshihikari, similar to the F1 hybrid line obtained from CMS-Koshihikari eichi 3go. Further, the F1 hybrid line obtained from CMS-Koshihikari kazusa 3go containing the Habataki-derived Gn1 gene exhibited a greater number of grains/spike than the F1 hybrid line obtained from CMS-Koshihikari, similar to the F1 hybrid line obtained from CMS-Koshihikari eichi 2go. The F1 hybrid line obtained from CMS-Koshihikari kazusa 2go containing the Habataki-derived Gn1 gene and the Habataki-derived hd1 gene exhibited slight late maturation as compared to Koshihikari which is an original cultivar, but showed greater numbers of grains/spike than Koshihikari in addition to exhibition of significantly early growth as compared to the F1 hybrid line obtained from CMS-Koshihikari.

From these results, it is clear that, with regard to a seed parent, similar to when each region was independently substituted, the effect of each region can be obtained also in the F1 hybrid even when plural regions were substituted.

TABLE 4

| Line | | | | | Days to |
| --- | --- | --- | --- | --- | --- |
| Seed parent | Substitution gene region | Pollen parent | Culm length (cm) | Number of grains/spike | heading (Day) |
| Koshihikari | — | | 99.6 ± 1.3 | 138.5 ± 3.8 | 104 |
| CMS-Koshihikari | — | ST-002 | 123.0 ± 0.9 | 284.0 ± 8.5 | 135 |

TABLE 4-continued

| Seed parent | Substitution gene region | Pollen parent | Culm length (cm) | Number of grains/spike | Days to heading (Day) |
|---|---|---|---|---|---|
| CMS-Koshihikari eichi 4go | sd1 | ST-002 | 106.9 ± 1.3 | 281.4 ± 9.3 | 135 |
| CMS-Koshihikari eichi 2go | Gn1 | ST-002 | 126.5 ± 2.0 | 314.8 ± 9.5 | 135 |
| CMS-Koshihikari kazusa 3go | sd1 & Gn1 | ST-002 | 103.5 ± 1.6 | 295.9 ± 6.7 | 134 |
| CMS-Koshihikari eichi 3go | hd1 | ST-002 | 95.1 ± 1.7 | 212.6 ± 8.7 | 107 |
| CMS-Koshihikari kazusa 1go | sd1 & hd1 | ST-002 | 86.8 ± 2.7 | 231.4 ± 5.4 | 109 |
| CMS-Koshihikari kazusa 2go | Gn1 & hd1 | ST-002 | 94.9 ± 0.9 | 249.9 ± 9.6 | 109 |

Example 2

<Evaluation of Taste Quality>

Seeds of each F1 hybrid were obtained by mating CMS-Koshihikari or CMS-Milky Queen as a seed parent with ST-1, ST-2 or ST-4 as a pollen parent. Brown rice obtained by cultivating the resulting F1 hybrid was subjected to a taste quality organoleptic test. In the taste quality organoleptic test, a blend of brown rice of Koshihikari cultivated in a plurality of producing areas was used as a control. The test results are given in Table 5. As a result, the overall taste quality value of brown rice of each F1 hybrid obtained from CMS-Koshihikari was equal to or slightly inferior to Koshihikari. On the other hand, the overall taste quality value of brown rice of each F1 hybrid obtained from CMS-Milky Queen was superior to the F1 hybrid obtained from CMS-Koshihikari. From the observation of a tendency showing that an item of glutinosity became strong, improvement of the overall taste quality value was believed to be due to the introduction of a semi-waxiness gene. Further, there was no significant difference in characteristics due to a difference of CMS lines, other than the difference in terms of a brown rice characteristic.

From these results, it is clear that, by using the rice cytoplasmic male sterile line exhibiting semi-waxiness as a seed parent, the taste quality of an F1 hybrid can be further improved as compared to when the rice cytoplasmic male sterile line exhibiting no semi-waxiness is used as a seed parent.

cultivar Kusahonami, *Oryza sativa* L. cultivar Takanari, *Oryza sativa* L. cultivar Nishiaoba, *Oryza sativa* L. cultivar Fukuhibiki, *Oryza sativa* L. cultivar Hoshiaoba, *Oryza sativa* L. cultivar Guichao 2, *Oryza sativa* L. cultivar Shui-Yuan 258, or *Oryza sativa* L. cultivar Yumeaoba as a pollen parent. The resulting F1 hybrids were cultivated, and days to heading thereof were investigated. As a control, Koshihikari and each pollen parent were also cultivated and days to heading thereof were investigated.

Figure 17:
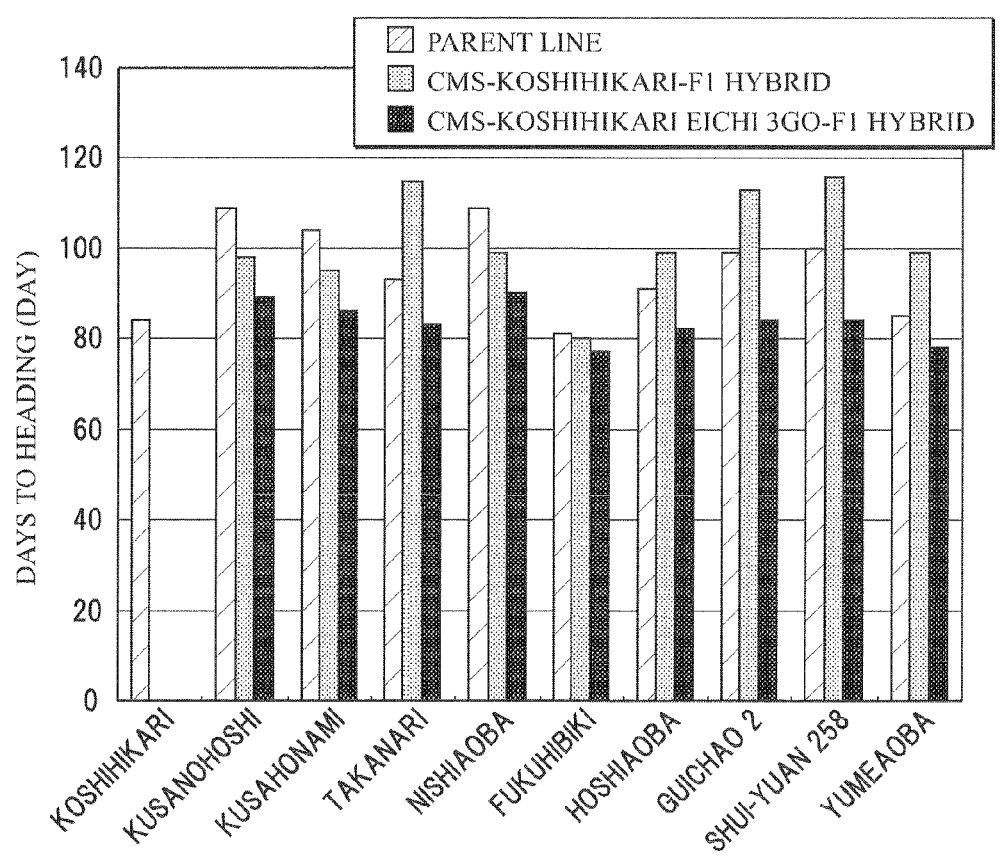
FIG. 17 is a view showing the measurement results of days to heading of each F1 hybrid and a pollen parent thereof, according to pollen parents, in Example 3.

The measurement results of days to heading of each line are shown in FIG. 17. In this test in which seeds were sowed on May 13, days to heading of the control cultivar Koshihikari were 84 days, whereas many of the F1 hybrid lines obtained by using the tested CMS-Koshihikari as a seed parent exhibited longer days to heading and conversion into late maturation, with an individual having days to heading of within 95 days being merely one line. On the other hand, all of the F1 hybrid lines obtained by using CMS-Koshihikari eichi 3go as a seed parent exhibited fewer days to heading and showed conversion into late maturation, as compared to the pollen parent or the F1 hybrid line obtained by using CMS-Koshihikari as a seed parent. In particular, all of the F1 hybrid lines obtained by using CMS-Koshihikari eichi 3go as a seed parent exhibited days to heading of within 90 days.

From these results, it is clear that, by using the rice male sterile line containing the Habataki-derived hd1 gene as a

TABLE 5

| | Overall judgment | | | | | | | |
|---|---|---|---|---|---|---|---|---|
| Name of line | Evaluation value | Confidence interval | Predominance difference | Appearance | Fragrances | Taste | Glutinosity | Rigidity |
| Koshihikari | 0.25 | ±0.198 | + | 0.20 | 0.15 | 0.30 | 0.05 | 0.10 |
| CMS-Koshihikari/ST-1 | −0.05 | ±0.313 | 0 | 0.05 | 0.10 | 0.00 | 0.30 | 0.25 |
| CMS-Milky Queen/ST-1 | 0.20 | ±0.313 | 0 | 0.05 | 0.20 | 0.15 | 0.45 | 0.25 |
| CMS-Koshihikari/ST-2 | 0.00 | ±0.257 | 0 | 0.15 | 0.15 | −0.15 | −0.35 | −0.20 |
| CMS-Milky Queen/ST-2 | 0.45 | ±0.257 | + | 0.35 | 0.30 | 0.45 | 0.55 | 0.15 |
| CMS-Koshihikari/ST-4 | −0.45 | ±0.278 | − | −0.25 | −0.20 | −0.55 | 0.00 | 0.10 |
| CMS-Milky Queen/ST-4 | 0.05 | ±0.278 | 0 | −0.15 | 0.00 | 0.00 | 0.60 | 0.25 |

Example 3

<Days to Heading of F1 Hybrid>

Seeds of each F1 hybrid were obtained by mating CMS-Koshihikari or CMS-Koshihikari eichi 3go as a seed parent with *Oryza sativa* L. cultivar Kusanohoshi, *Oryza sativa* L.

seed parent, conversion of an F1 hybrid to have earlier growth can be achieved as compared to when CMS-Koshihikari is used as a seed parent, and therefore efficiency of selection is remarkably improved in breeding of a line having a period of maturity close to Koshihikari.

INDUSTRIAL APPLICABILITY

The method for producing a rice F1 seed in accordance with the present invention is capable of producing a seed of a rice F1 hybrid with higher efficiency of selection, as compared to when a male sterile line of *Oryza sativa* L. cultivar Koshihikari is used as a seed parent, and therefore the method can be utilized, particularly, in the field of plant breeding.

SEQUENCE LIST

[FIG. 1]
 HABATAKI-DERIVED CHROMOSOME FRAGMENT
 KOSHIHIKARI CHROMOSOME
[FIG. 2]
 HABATAKI-DERIVED CHROMOSOME FRAGMENT
 KOSHIHIKARI CHROMOSOME
[FIG. 3]
 HABATAKI-DERIVED CHROMOSOME FRAGMENT
 KOSHIHIKARI CHROMOSOME
[FIG. 4]
 HABATAKI-DERIVED CHROMOSOME FRAGMENT
 KOSHIHIKARI-DERIVED CHROMOSOME FRAGMENT
[FIG. 5]
 HABATAKI-DERIVED CHROMOSOME FRAGMENT
 KOSHIHIKARI-DERIVED CHROMOSOME FRAGMENT
[FIG. 6]
 HABATAKI-DERIVED CHROMOSOME FRAGMENT
 KOSHIHIKARI-DERIVED CHROMOSOME FRAGMENT
[FIG. 7]
 HABATAKI-DERIVED CHROMOSOME FRAGMENT
 KOSHIHIKARI-DERIVED CHROMOSOME FRAGMENT
[FIG. 8]
 HABATAKI-DERIVED CHROMOSOME FRAGMENT
 KOSHIHIKARI-DERIVED CHROMOSOME FRAGMENT
[FIG. 9]
 HABATAKI-DERIVED CHROMOSOME FRAGMENT
 KOSHIHIKARI-DERIVED CHROMOSOME FRAGMENT
[FIG. 10]
 HABATAKI-DERIVED CHROMOSOME FRAGMENT
 KOSHIHIKARI-DERIVED CHROMOSOME FRAGMENT
[FIG. 11]
 HABATAKI-DERIVED CHROMOSOME FRAGMENT
 KOSHIHIKARI-DERIVED CHROMOSOME FRAGMENT
[FIG. 12]
 CULM LENGTH (cm)
 KOSHIHIKARI
 CMS-KOSHIHIKARI-F1 HYBRID
 CMS-KOSHIHIKARI EICHI 4GO-F1 HYBRID
[FIG. 13]
 CULM LENGTH (cm)
 KOSHIHIKARI
 CMS-KOSHIHIKARI/ST-1
 CMS-KOSHIHIKARI EICHI 4GO/ST-1
 CMS-KOSHIHIKARI EICHI 4GO_LONG REGION/ST-1
[FIG. 14]
 DAYS TO HEADING (DAY)
 KOSHIHIKARI
 CMS-KOSHIHIKARI-F1 HYBRID
 CMS-KOSHIHIKARI EICHI 3GO-F1 HYBRID
[FIG. 15]
 NUMBER OF GRAINS/SPIKE
 KOSHIHIKARI
 CMS-KOSHIHIKARI-F1 HYBRID
 CMS-KOSHIHIKARI EICHI 2GO-F1 HYBRID
[FIG. 16]
 NUMBER OF GRAINS/SPIKE
 KOSHIHIKARI
 CMS-KOSHIHIKARI/ST-2
 CMS-KOSHIHIKARI EICHI 2GO/ST-2
 CMS-KOSHIHIKARI EICHI 2GO_LONG REGION/ST-2
[FIG. 17]
 DAYS TO HEADING (DAY)
 PARENT LINE
 CMS-KOSHIHIKARI-F1 HYBRID
 CMS-KOSHIHIKARI EICHI 3GO-F1 HYBRID
 KOSHIHIKARI, KUSANOHOSHI, KUSAHONAMI, TAKANARI, NISHIAOBA, FUKUHIBIKI, HOSHIAOBA, GUICHAO 2, SHUI-YUAN 258, YUMEAOBA

What is claimed is:

1. A method for producing a rice F1 seed, comprising:
crossing a cytoplasmic male sterile line of rice selected from the group consisting of a rice cytoplasmic male sterile line CMS-Koshihikari eichi 2go, a rice cytoplasmic male sterile line CMS-Koshihikari eichi 3go, a rice cytoplasmic male sterile line CMS-Koshihikari eichi 4go, a rice cytoplasmic male sterile line CMS-Koshihikari kazusa 1go, a rice cytoplasmic male sterile line CMS-Koshihikari kazusa 2go, and a rice cytoplasmic male sterile line CMS-Koshihikari kazusa 3go as a seed parent, with a rice fertility restorer line as a pollen parent; and
collecting the first filial generation seed (F1 seed) from the post-crossing seed parent;
wherein representative seeds of said rice cytoplasmic male sterile lines CMS-Koshihikari eichi 2go, CMS-Koshihikari eichi 3go, CMS- Koshihikari eichi 4go, CMS-Koshihikari kazusa 1go, CMS-Koshihikari kazusa 2go, and CMS-Koshihikari kazusa 3go are deposited under accession numbers FERM ABP-22217, FERM ABP-22280, FERM ABP-22322, FERM ABP-22323, FERM ABP-22303, and FERM ABP-22218, respectively.

2. The method for producing a rice F1 seed according to claim 1, wherein the rice cytoplasmic male sterile line is selected from the group consisting of a rice cytoplasmic male sterile line CMS-Koshihikari eichi 2go, a rice cytoplasmic male sterile line CMS-Koshihikari eichi 3go, a rice cytoplasmic male sterile line CMS-Koshihikari eichi 4go, a rice cytoplasmic male sterile line CMS-Koshihikari kazusa 1go, and a rice cytoplasmic male sterile line CMS-Koshihikari kazusa 3go.

3. A rice cytoplasmic male sterile line CMS-Koshihikari eichi 2go, wherein representative seed of said line is deposited under Accession No. FERM ABP-22217.

4. A rice cytoplasmic male sterile line CMS-Koshihikari eichi 3go, wherein representative seed of said line is deposited under Accession No. FERM ABP-22280.

5. A rice cytoplasmic male sterile line CMS-Koshihikari eichi 4go, wherein a representative seed of said line is deposited under accession number FERM ABP-22322.

6. A rice cytoplasmic male sterile line CMS-Koshihikari kazusa 1go, wherein a representative seed of said line is deposited under accession number FERM ABP-22323.

7. A rice cytoplasmic male sterile line CMS-Koshihikari kazusa 2go, wherein a representative seed of said line is deposited under accession number FERM ABP-22303.

8. A rice cytoplasmic male sterile line CMS-Koshihikari kazusa 3go, wherein a representative seed of said line is deposited under accession number FERM ABP-22218.

* * * * *

SEQUENCE LISTING

```
<160> NUMBER OF SEQ ID NOS: 61

<210> SEQ ID NO 1
<211> LENGTH: 20
<212> TYPE: DNA
<213> ORGANISM: Oryza sativa
<220> FEATURE:
<223> OTHER INFORMATION: DNA marker: Upper Sequence of SP-2058

<400> SEQUENCE: 1
tgctacaact gtacacactg                                               20

<210> SEQ ID NO 2
<211> LENGTH: 20
<212> TYPE: DNA
<213> ORGANISM: Oryza sativa
<220> FEATURE:
<223> OTHER INFORMATION: DNA marker: Lower Sequence of SP-2058
```

```
<400> SEQUENCE: 2
gctcgaagac acattggttc                                                 20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      rice SNP primer of SP-2058

<400> SEQUENCE: 3
agtagaaaaa ccaacacctt                                                 20

<210> SEQ ID NO 4
<211> LENGTH: 19
<212> TYPE: DNA
<213> ORGANISM: Oryza sativa
<220> FEATURE:
<223> OTHER INFORMATION: DNA marker: Upper Sequence of SP-4009

<400> SEQUENCE: 4
ccgttatgtg cctgtatgg                                                  19

<210> SEQ ID NO 5
<211> LENGTH: 20
<212> TYPE: DNA
<213> ORGANISM: Oryza sativa
<220> FEATURE:
<223> OTHER INFORMATION: DNA marker: Lower Sequence of SP-4009

<400> SEQUENCE: 5
tgttgcagga aggtgacagg                                                 20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      rice SNP primer of SP-4009

<400> SEQUENCE: 6
ttggaaggaa catctagcac a                                               21

<210> SEQ ID NO 7
<211> LENGTH: 18
<212> TYPE: DNA
<213> ORGANISM: Oryza sativa
<220> FEATURE:
<223> OTHER INFORMATION: DNA marker: Upper Sequence of G2003

<400> SEQUENCE: 7
cacagcgctc acttctca                                                   18

<210> SEQ ID NO 8
<211> LENGTH: 20
<212> TYPE: DNA
<213> ORGANISM: Oryza sativa
<220> FEATURE:
<223> OTHER INFORMATION: DNA marker: Lower Sequence of G2003

<400> SEQUENCE: 8
tgcaatgtcg tccaccatcg                                                 20
```

```
<210> SEQ ID NO 9
<211> LENGTH: 18
<212> TYPE: DNA
<213> ORGANISM: Oryza sativa
<220> FEATURE:
<223> OTHER INFORMATION: DNA marker: Upper Sequence of G2002

<400> SEQUENCE: 9
cacagcgctc acttctca                                                 18

<210> SEQ ID NO 10
<211> LENGTH: 19
<212> TYPE: DNA
<213> ORGANISM: Oryza sativa
<220> FEATURE:
<223> OTHER INFORMATION: DNA marker: Lower Sequence of G2002

<400> SEQUENCE: 10
atgatcgtca gcgacagct                                                19

<210> SEQ ID NO 11
<211> LENGTH: 18
<212> TYPE: DNA
<213> ORGANISM: Oryza sativa
<220> FEATURE:
<223> OTHER INFORMATION: DNA marker: Upper Sequence of SP-462

<400> SEQUENCE: 11
aactccagcg tgctaagc                                                 18

<210> SEQ ID NO 12
<211> LENGTH: 18
<212> TYPE: DNA
<213> ORGANISM: Oryza sativa
<220> FEATURE:
<223> OTHER INFORMATION: DNA marker: Lower Sequence of SP-462

<400> SEQUENCE: 12
gcattgcatg caggatcg                                                 18

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      rice SNP primer of SP-462

<400> SEQUENCE: 13
agagcccttc actttcagc                                                19

<210> SEQ ID NO 14
<211> LENGTH: 18
<212> TYPE: DNA
<213> ORGANISM: Oryza sativa
<220> FEATURE:
<223> OTHER INFORMATION: DNA marker: Upper Sequence of SP-1259

<400> SEQUENCE: 14
aaggctgatg agcactgc                                                 18

<210> SEQ ID NO 15
<211> LENGTH: 19
<212> TYPE: DNA
<213> ORGANISM: Oryza sativa
<220> FEATURE:
<223> OTHER INFORMATION: DNA marker: Lower Sequence of SP-1259
```

<400> SEQUENCE: 15
ggcattgtgg aagctcttc                                                    19

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence: Synthetic
      rice SNP primer of SP-1259

<400> SEQUENCE: 16
tctcctttcg gagtccc                                                      17

<210> SEQ ID NO 17
<211> LENGTH: 22
<212> TYPE: DNA
<213> ORGANISM: Oryza sativa
<220> FEATURE:
<223> OTHER INFORMATION: DNA marker: Upper Sequence of SP-477

<400> SEQUENCE: 17
gctatgttga acaagttcgc tg                                                22

<210> SEQ ID NO 18
<211> LENGTH: 20
<212> TYPE: DNA
<213> ORGANISM: Oryza sativa
<220> FEATURE:
<223> OTHER INFORMATION: DNA marker: Lower Sequence of SP-477

<400> SEQUENCE: 18
catcgtggac agcaatcttg                                                   20

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      rice SNP primer of SP-477

<400> SEQUENCE: 19
gtatagttag tcatgtgcc                                                    19

<210> SEQ ID NO 20
<211> LENGTH: 20
<212> TYPE: DNA
<213> ORGANISM: Oryza sativa
<220> FEATURE:
<223> OTHER INFORMATION: DNA marker: Upper Sequence of SP-156

<400> SEQUENCE: 20
ggaattcaga gacaacatgg                                                   20

<210> SEQ ID NO 21
<211> LENGTH: 22
<212> TYPE: DNA
<213> ORGANISM: Oryza sativa
<220> FEATURE:
<223> OTHER INFORMATION: DNA marker: Lower Sequence of SP-156

<400> SEQUENCE: 21
gcttcagtgt tgtgtgattc tg                                                22

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic rice SNP primer of SP-156

<400> SEQUENCE: 22
aacgagttct acaatgctgc                                              20

<210> SEQ ID NO 23
<211> LENGTH: 21
<212> TYPE: DNA
<213> ORGANISM: Oryza sativa
<220> FEATURE:
<223> OTHER INFORMATION: DNA marker: Upper Sequence of SP-2032

<400> SEQUENCE: 23
cattgagtcc atttcctctg c                                            21

<210> SEQ ID NO 24
<211> LENGTH: 20
<212> TYPE: DNA
<213> ORGANISM: Oryza sativa
<220> FEATURE:
<223> OTHER INFORMATION: DNA marker: Lower Sequence of SP-2032

<400> SEQUENCE: 24
gcagctccaa gaatgactac                                              20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic rice SNP primer of SP-2032

<400> SEQUENCE: 25
attggtgcta gagcaactac                                              20

<210> SEQ ID NO 26
<211> LENGTH: 20
<212> TYPE: DNA
<213> ORGANISM: Oryza sativa
<220> FEATURE:
<223> OTHER INFORMATION: DNA marker: Upper Sequence of SP-170

<400> SEQUENCE: 26
gtgagacata gactatccac                                              20

<210> SEQ ID NO 27
<211> LENGTH: 19
<212> TYPE: DNA
<213> ORGANISM: Oryza sativa
<220> FEATURE:
<223> OTHER INFORMATION: DNA marker: Lower Sequence of SP-170

<400> SEQUENCE: 27
acgcgtacgc cacatagac                                               19

<210> SEQ ID NO 28
<211> LENGTH: 19
<212> TYPE: DNA
<213> ORGANISM: Artificial Sequence

```
<220> FEATURE:
<223> OTHER INFORMATION: Description of Artificial Sequence: Synthetic
      rice SNP primer of SP-170

<400> SEQUENCE: 28
agggtgagga atgtccggt                                                  19

<210> SEQ ID NO 29
<211> LENGTH: 20
<212> TYPE: DNA
<213> ORGANISM: Oryza sativa
<220> FEATURE:
<223> OTHER INFORMATION: DNA marker: Upper Sequence of SP-4028

<400> SEQUENCE: 29
gcagtacctg ccttactacg                                                 20

<210> SEQ ID NO 30
<211> LENGTH: 20
<212> TYPE: DNA
<213> ORGANISM: Oryza sativa
<220> FEATURE:
<223> OTHER INFORMATION: DNA marker: Lower Sequence of SP-4028

<400> SEQUENCE: 30
catttcatgc gagtggtgac                                                 20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      rice SNP primer of SP-4028

<400> SEQUENCE: 31
tgcacgaatc ttggccagag                                                 20

<210> SEQ ID NO 32
<211> LENGTH: 24
<212> TYPE: DNA
<213> ORGANISM: Oryza sativa
<220> FEATURE:
<223> OTHER INFORMATION: DNA marker: Upper Sequence of SP-4038

<400> SEQUENCE: 32
cttaaactca acttgcacaa gtag                                            24

<210> SEQ ID NO 33
<211> LENGTH: 20
<212> TYPE: DNA
<213> ORGANISM: Oryza sativa
<220> FEATURE:
<223> OTHER INFORMATION: DNA marker: Lower Sequence of SP-4038

<400> SEQUENCE: 33
actgccgaca tgttactgtc                                                 20

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      rice SNP primer of SP-4038

<400> SEQUENCE: 34
```

```
gtcccacctg aaacatatcc a                                           21

<210> SEQ ID NO 35
<211> LENGTH: 22
<212> TYPE: DNA
<213> ORGANISM: Oryza sativa
<220> FEATURE:
<223> OTHER INFORMATION: DNA marker: Upper Sequence of SP-4030

<400> SEQUENCE: 35
tctttgattc tttggtcgat cg                                          22

<210> SEQ ID NO 36
<211> LENGTH: 20
<212> TYPE: DNA
<213> ORGANISM: Oryza sativa
<220> FEATURE:
<223> OTHER INFORMATION: DNA marker: Lower Sequence of SP-4030

<400> SEQUENCE: 36
gcgtacgaga gctatagagc                                             20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      rice SNP primer of SP-4030

<400> SEQUENCE: 37
atggatccgt ggatcgatcg                                             20

<210> SEQ ID NO 38
<211> LENGTH: 20
<212> TYPE: DNA
<213> ORGANISM: Oryza sativa
<220> FEATURE:
<223> OTHER INFORMATION: DNA marker: Upper Sequence of SP-262

<400> SEQUENCE: 38
gcagcaggac aaaggctaac                                             20

<210> SEQ ID NO 39
<211> LENGTH: 20
<212> TYPE: DNA
<213> ORGANISM: Oryza sativa
<220> FEATURE:
<223> OTHER INFORMATION: DNA marker: Lower Sequence of SP-262

<400> SEQUENCE: 39
acccttcttc aagctccatc                                             20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      rice SNP primer of SP-262

<400> SEQUENCE: 40
tcacaaccgg accagatgac                                             20

<210> SEQ ID NO 41
```

```
<211> LENGTH: 21
<212> TYPE: DNA
<213> ORGANISM: Oryza sativa
<220> FEATURE:
<223> OTHER INFORMATION: DNA marker: Upper Sequence of SP-2229

<400> SEQUENCE: 41
caatctggga ttctggatca g                                            21

<210> SEQ ID NO 42
<211> LENGTH: 20
<212> TYPE: DNA
<213> ORGANISM: Oryza sativa
<220> FEATURE:
<223> OTHER INFORMATION: DNA marker: Lower Sequence of SP-2229

<400> SEQUENCE: 42
agctcagtat cacggacttg                                              20

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      rice SNP primer of SP-2229

<400> SEQUENCE: 43
gtctctttta acacacctta c                                            21

<210> SEQ ID NO 44
<211> LENGTH: 22
<212> TYPE: DNA
<213> ORGANISM: Oryza sativa
<220> FEATURE:
<223> OTHER INFORMATION: DNA marker: Upper Sequence of SP-2513

<400> SEQUENCE: 44
gcgaaaagat gaggatgtac ac                                           22

<210> SEQ ID NO 45
<211> LENGTH: 20
<212> TYPE: DNA
<213> ORGANISM: Oryza sativa
<220> FEATURE:
<223> OTHER INFORMATION: DNA marker: Lower Sequence of SP-2513

<400> SEQUENCE: 45
ccgtaggcct ttgtcaagtg                                              20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      rice SNP primer of SP-2513

<400> SEQUENCE: 46
ctttaatggt ggcttatgtc                                              20

<210> SEQ ID NO 47
<211> LENGTH: 22
<212> TYPE: DNA
<213> ORGANISM: Oryza sativa
<220> FEATURE:
<223> OTHER INFORMATION: DNA marker: Upper Sequence of SP-586
```

```
<400> SEQUENCE: 47
gctaggacaa gcttatttca gc                                              22

<210> SEQ ID NO 48
<211> LENGTH: 18
<212> TYPE: DNA
<213> ORGANISM: Oryza sativa
<220> FEATURE:
<223> OTHER INFORMATION: DNA marker: Lower Sequence of SP-586

<400> SEQUENCE: 48
tcacgccgat caagaacg                                                   18

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic
      rice SNP primer of SP-586

<400> SEQUENCE: 49
cataatttat cgccattttc gcat                                            24

<210> SEQ ID NO 50
<211> LENGTH: 18
<212> TYPE: DNA
<213> ORGANISM: Oryza sativa
<220> FEATURE:
<223> OTHER INFORMATION: DNA marker: Upper Sequence of SP-2254

<400> SEQUENCE: 50
aggcccttgt actggtac                                                   18

<210> SEQ ID NO 51
<211> LENGTH: 21
<212> TYPE: DNA
<213> ORGANISM: Oryza sativa
<220> FEATURE:
<223> OTHER INFORMATION: DNA marker: Lower Sequence of SP-2254

<400> SEQUENCE: 51
gtacacaata gttggtgcac c                                               21

<210> SEQ ID NO 52
<211> LENGTH: 19
<212> TYPE: DNA
<213> ORGANISM: Artificial Sequence
<220> FEATURE:
<223> OTHER INFORMATION: Description of Artificial Sequence: Synthetic
      rice SNP primer of SP-2254

<400> SEQUENCE: 52
catgataagg tactcctgg                                                  19

<210> SEQ ID NO 53
<211> LENGTH: 22
<212> TYPE: DNA
<213> ORGANISM: Oryza sativa
<220> FEATURE:
<223> OTHER INFORMATION: DNA marker: Upper Sequence of SP-1603

<400> SEQUENCE: 53
cctagtccct aaagatctca tg                                              22
```

<210> SEQ ID NO 54
<211> LENGTH: 21
<212> TYPE: DNA
<213> ORGANISM: Oryza sativa
<220> FEATURE:
<223> OTHER INFORMATION: DNA marker: Lower Sequence of SP-1603

<400> SEQUENCE: 54
gatagacatg acggagaagt g                                      21

<210> SEQ ID NO 55
<211> LENGTH: 19
<212> TYPE: DNA
<213> ORGANISM: Artificial Sequence
<220> FEATURE:
<223> OTHER INFORMATION: Description of Artificial Sequence: Synthetic
      rice SNP primer of SP-1603

<400> SEQUENCE: 55
gggtggtgtt atctctagt                                         19

<210> SEQ ID NO 56
<211> LENGTH: 20
<212> TYPE: DNA
<213> ORGANISM: Oryza sativa
<220> FEATURE:
<223> OTHER INFORMATION: DNA marker: Upper Sequence of SP-604

<400> SEQUENCE: 56
gcgcaaattc cttcagtcac                                        20

<210> SEQ ID NO 57
<211> LENGTH: 19
<212> TYPE: DNA
<213> ORGANISM: Oryza sativa
<220> FEATURE:
<223> OTHER INFORMATION: DNA marker: Lower Sequence of SP-604

<400> SEQUENCE: 57
cagtttcagg tggaagacc                                         19

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Synthetic
      rice SNP primer of SP-604

<400> SEQUENCE: 58
caagtttctt cctctcattt tc                                     22

<210> SEQ ID NO 59
<211> LENGTH: 20
<212> TYPE: DNA
<213> ORGANISM: Oryza sativa
<220> FEATURE:
<223> OTHER INFORMATION: DNA marker: Upper Sequence of SP-1635

<400> SEQUENCE: 59
taggagtgaa tggcggtaag                                        20

<210> SEQ ID NO 60
<211> LENGTH: 22
<212> TYPE: DNA
<213> ORGANISM: Oryza sativa

```
<220> FEATURE:
<223> OTHER INFORMATION: DNA marker: Lower Sequence of SP-1635

<400> SEQUENCE: 60
gtatatcccg acaatagtcc tg                                              22

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence: Synthetic
      rice SNP primer of SP-1635

<400> SEQUENCE: 61
gtacatgata atacagcaaa gatt                                            24
```